(12) United States Patent
Dashper et al.

(10) Patent No.: US 8,916,166 B2
(45) Date of Patent: Dec. 23, 2014

(54) PORPHYROMONAS GINGIVALIS POLYPEPTIDES USEFUL IN THE PREVENTION OF PERIODONTAL DISEASE

(75) Inventors: Stuart Geoffrey Dashper, Victoria (AU); Ching Seng Ang, Victoria (AU); Paul David Veith, Victoria (AU); Eric Charles Reynolds, Victoria (AU)

(73) Assignee: Oral Health Australia Pty Ltd, Carlton, Victoria (AU)

( * ) Notice: Subject to any disclaimer, the term of this patent is extended or adjusted under 35 U.S.C. 154(b) by 146 days.

(21) Appl. No.: 13/547,556

(22) Filed: Jul. 12, 2012

(65) Prior Publication Data

US 2013/0236488 A1    Sep. 12, 2013

Related U.S. Application Data

(62) Division of application No. 12/306,495, filed as application No. PCT/AU2007/000890 on Jun. 27, 2007, now abandoned.

(30) Foreign Application Priority Data

Jun. 27, 2006   (AU) ................................ 2006903425

(51) Int. Cl.
| | | |
|---|---|---|
| A61K 39/02 | (2006.01) | |
| C07K 14/195 | (2006.01) | |
| A61K 38/16 | (2006.01) | |
| A61K 39/00 | (2006.01) | |

(52) U.S. Cl.
CPC ........... *A61K 39/0216* (2013.01); *A61K 38/164* (2013.01); *C07K 14/195* (2013.01); *A61K 39/00* (2013.01); *G01N 2333/195* (2013.01); *G01N 2800/18* (2013.01)
USPC ...................... 424/190.1; 424/234.1; 530/350

(58) Field of Classification Search
CPC ..... C07K 14/195; A61K 39/00; A61K 38/00; A61K 39/0208
USPC .............................. 530/350; 424/190.1, 234.1
See application file for complete search history.

(56) References Cited

U.S. PATENT DOCUMENTS

| | | | |
|---|---|---|---|
| 4,603,112 A | 7/1986 | Paoletti et al. | |
| 4,735,801 A | 4/1988 | Stocker | |
| 4,837,151 A | 6/1989 | Stocker | |
| 5,210,035 A | 5/1993 | Stocker | |
| 5,475,097 A | 12/1995 | Travis et al. | |
| 5,523,390 A | 6/1996 | Travis et al. | |
| 5,707,620 A | 1/1998 | Travis et al. | |
| 5,711,937 A | 1/1998 | Nishida et al. | |
| 6,129,917 A | 10/2000 | Potempa et al. | |
| 6,274,718 B1 | 8/2001 | Travis et al. | |
| 6,444,799 B1 | 9/2002 | Ross | |
| 6,511,666 B1 | 1/2003 | Reynolds et al. | |
| 6,528,038 B1 | 3/2003 | Reynolds et al. | |
| 6,576,226 B1 | 6/2003 | Jernberg | |
| 6,962,706 B1 | 11/2005 | O'Brien-Simpson et al. | |
| 7,204,991 B2 | 4/2007 | Barr et al. | |
| 7,262,271 B2 | 8/2007 | Reynolds et al. | |
| 7,341,727 B1 | 3/2008 | Tucker et al. | |
| 7,419,671 B2 * | 9/2008 | Reynolds et al. ........... 424/190.1 |
| 7,544,777 B2 | 6/2009 | Ross et al. | |
| 7,749,502 B2 | 7/2010 | Reynolds et al. | |
| 8,241,611 B2 | 8/2012 | Dashper et al. | |
| 2005/0288866 A1 | 12/2005 | Sachdeva et al. | |
| 2008/0175867 A1 | 7/2008 | Reynolds et al. | |
| 2010/0034908 A1 | 2/2010 | Ross et al. | |
| 2010/0209362 A1 | 8/2010 | Dashper et al. | |
| 2010/0297179 A1 | 11/2010 | Dashper et al. | |
| 2011/0081358 A1 | 4/2011 | Reynolds et al. | |
| 2011/0104179 A1 | 5/2011 | Reynolds et al. | |
| 2011/0213129 A1 | 9/2011 | Reynolds et al. | |
| 2011/0280880 A1 | 11/2011 | Reynolds et al. | |
| 2013/0028847 A1 | 1/2013 | Dashper et al. | |
| 2013/0202641 A1 | 8/2013 | Dashper et al. | |

FOREIGN PATENT DOCUMENTS

| | | |
|---|---|---|
| GB | 2 381 449 | 5/2003 |
| WO | WO 94/27606 | 12/1994 |
| WO | WO 95/07286 | 3/1995 |
| WO | WO 95/09181 A1 | 4/1995 |
| WO | WO 95/11298 | 4/1995 |
| WO | WO 95/26404 A1 | 10/1995 |
| WO | WO 96/17936 | 6/1996 |
| WO | WO 97/34629 A1 | 9/1997 |
| WO | WO 00/75346 A1 | 12/2000 |
| WO | WO 96/17936 A2 | 3/2005 |
| WO | WO 2005/019249 | 3/2005 |
| WO | WO 2008/016385 | 2/2008 |
| WO | WO 2008/124646 A2 | 10/2008 |

OTHER PUBLICATIONS

Houghten et al. (Vaccines, 1986, Edited by Fred Brown: Cold Spring Harbor Laboratory).*
International Search Report issued on Sep. 12, 2008 in application No. PCT/AU2008/001018.
Supplementary Search Report issued on Feb. 9, 2011 in application No. EP 08 77 2643.
International Search Report issued on Nov. 1, 2005 in application No. PCT/AU2005/001463 (corresponding to US 2009/0175867 and US 2011/0081358).
International Search Report issued on Aug. 17, 2007 in application No. PCT/AU2007/000890 (corresponding to US 2010/0092471).
International Search Report issued on Oct. 13, 2009 in application No. PCT/AU2009/001112 (corresponding to U.S. Appl. No. 13/060,653).
International Search Report issued on Jan. 31, 1997 in application No. PCT/AU96/00673 (corresponding to US 6,511,666 and US 2007/0189982).
International Search Report issued on Jan. 28, 1999 in application No. PCT/AU98/01023 (corresponding to US 7,544,777 and US 2010/0034908).

(Continued)

*Primary Examiner* — Padma V Baskar
(74) *Attorney, Agent, or Firm* — Foley & Lardner LLP

(57) ABSTRACT

The invention is directed to vaccine compositions and methods based on *P. gingivalis* proteins identified to be regulated by haem availability that can be used in the prevention and treatment of periodontal disease. In particular, two specific internalin-like *P. gingivalis* proteins, namely PG0350 and PG1374 involved in the internalization of *P. gingivalis* by host cells, the hypothetical protein, PG1019 purported to be a cell surface lipoprotein and the alkyl hydroperoxide reductase protein, PG0618 have been identified as useful targets for the prevention and treatment of periodontal disease.

8 Claims, 9 Drawing Sheets

(56) References Cited

OTHER PUBLICATIONS

International Search Report issued on Sep. 12, 2008 in application No. PCT/AU2008/001017 (corresponding to US 2010/0297179).
Office Action issued on Mar. 15, 2012 by the Examiner in U.S. Appl. No. 12/306,495 (US 2010/0092471).
Office Action issued on Feb. 22, 2012 by the Examiner in U.S. Appl. No. 12/306,495 (US 2010/0092471).
Office Action issued on Sep. 16, 2011 by the Examiner in U.S. Appl. No. 12/306,495 (US 2010/0092471).
Office Action issued on Dec. 27, 2010 by the Examiner in U.S. Appl. No. 12/306,495 (US 2010/0092471).
Office Action issued on Jun. 3, 2010 by the Examiner in U.S. Appl. No. 12/306,495 (US 2010/0092471).
Office Action issued on Mar. 23, 2010 by the Examiner in U.S. Appl. No. 12/306,495 (US 2010/0092471).
Notice of Allowance issued on Dec. 5, 2008 by the Examiner in U.S. Appl. No. 11/589,261 (US 7,544,777).
Office Action issued on May 19, 2008 by the Examiner in U.S. Appl. No. 11/589,261 (US 7,544,777).
Office Action issued on Oct. 30, 2007 by the Examiner in U.S. Appl. No. 11/589,261 (US 7,544,777).
Office Action issued on Apr. 28, 2006 by the Examiner in U.S. Appl. No. 09/581,286.
Office Action issued on Sep. 16, 2005 by the Examiner in U.S. Appl. No. 09/581,286.
Office Action issued on Mar. 24, 2005 by the Examiner in U.S. Appl. No. 09/581,286.
Office Action issued on Aug. 25, 2004 by the Examiner in U.S. Appl. No. 09/581,286.
Office Action issued on Jan. 27, 2004 by the Examiner in U.S. Appl. No. 09/581,286.
Office Action issued on Oct. 1, 2002 by the Examiner in U.S. Appl. No. 09/581,286.
Office Action issued on May 17, 2011 by the Examiner in U.S. Appl. No. 12/382,845 (US 2010/0034908).
Office Action issued on Nov. 2, 2010 by the Examiner in U.S. Appl. No. 12/382,845 (US 2010/0034908).
Office Action issued on Sep. 17, 2010 by the Examiner in U.S. Appl. No. 11/654,512 (US 2007/0189982).
Office Action issued on Aug. 12, 2009 by the Examiner in U.S. Appl. No. 11/654,512 (US 2007/0189982).
Office Action issued on Oct. 23, 2008 by the Examiner in U.S. Appl. No. 11/654,512 (US 2007/0189982).
Office Action issued on Feb. 7, 2008 by the Examiner in U.S. Appl. No. 11/654,512 (US 2007/0189982).
Office Action issued on Aug. 21, 2007 by the Examiner in U.S. Appl. No. 11/654,512 (US 2007/0189982).
Office Action issued on Dec. 21, 2011 by the Examiner in U.S. Appl. No. 11/729,218 (US 2008/0175867).
Office Action issued on Oct. 29, 2009 by the Examiner in U.S. Appl. No. 11/729,218 (US 2008/0175867).
Office Action issued on Apr. 10, 2009 by the Examiner in U.S. Appl. No. 11/729,218 (US 2008/0175867).
Office Action issued on Aug. 28, 2008 by the Examiner in U.S. Appl. No. 11/729,218 (US 2008/0175867).
Office Action issued on May 12, 2010 by the Examiner in U.S. Appl. No. 11/663,671 (US 2009/0169568).
Office Action issued on Nov. 4, 2009 by the Examiner in U.S. Appl. No. 11/663,671 (US 2009/0169568).
Office Action issued on Jul. 9, 2010 by the Examiner in U.S. Appl. No. 12/382,845 (US 2010/0034908).
Notice of Allowance issued by the Examiner on Nov. 1, 2011 in U.S. Appl. No. 12/382,845 (US 2010/0034908).
Office Action issued by the Examiner on Nov. 2, 2010 in U.S. Appl. No. 12/382,845 (US 2010/0034908).
Office Action issued by the Examiner on Jul. 9, 2010 in U.S. Appl. No. 12/382,845 (US 2010/0034908).
Office Action issued by the Examiner on Nov. 25, 2011 in U.S. Appl. No. 12/668,652 (US 2010/0209362).

Rosenstein et al., "Hypothesis: The Humoral Immune Response to Oral Bacteria Provides a Stimulus for the Development of Rheumatoid Arthritis," Inflammation, vol. 28, No. 6, pp. 311-18, 2004.
McGraw et al., "Purification, Characterization, and Sequence Analysis of a Potential Virulence Factor from *Porphyromonas gingivalis*, Peptidylarginine Deiminase," Infection and Immunity, vol. 67, No. 7, pp. 3248-3256, Jul. 1999.
Kyte et al., "A simple method for displaying the hydropathic character of a protein," *Journal of Molecular Biology*, vol. 157, Issue 1, pp. 105-132, May 1982, Abstract.
Aduse Opoku et al., "Characterization, Genetic Analysis, and Expression of a Protease Antigen (PrpRl) of *Porphyromonas gingivalis* W50," Infection & Immunity, vol. 63, No. 12, pp. 4744-4754, Dec. 1995.
Barkocy-Gallagher et al., "Analysis of the *prtP* Gene Encoding Porphypain, a Cysteine Proteinase of *Porphyromonas gingivalis*," *J. of Bacteriolgy*, vol. 178, No. 10, May 1996.
Bedi, "Comparative Study of Four Proteases from Spent Culture Media of *Porphyromonas gingivalis* (FAY-19M-1)," *Preparative Biochemistry*, pp. 133-154, Aug. 1995.
Ciborowski, "Purification and Characterization of Two Forms of a High-Molecular-Weight Cysteine (Porphypain) from *Porphyromonas gingivalis*," *J. of Bacteriology*, pp. 4549-4557, 1994.
Okamoto et al., "Structural Characterization of Argingipain, a Novel Arginine-Specific Cysteine Proteinase as a Major Periodontal Pathogenic Factor from *Porphyromonas gingivalis*," *Archives of Biochemistry & Biophysics*, vol. 316, No. 2, pp. 917-925, Feb. 1, 1995.
Pavloff et al., "Molecular Cloning and Structural Characterization of the Arg-gingipain Proteinase of *Porphyromonas gingivalis*," *J. of Biol. Chem.*, vol. 270, No. 3, pp. 1007-1010, Jan. 20, 1995.
Pike et al., "Lysine- and Arginine-specific Proteinases from *Porphyromonas gingivalis*," *J. of Biol. Chem.*, vol. 269, No. 1, pp. 406-411, Jan. 7, 1994.
Slakeski et al., "Characterization of a *Porphyromnas gingivalis* Gene prtR That Encodes an Arginine-Specific Thiol Porteinase and Multiple Adhesins," *Biochem. & Biophys. Res. Comm.*, vol. 224, pp. 605-610, 1996.
Yoshimura, "Characterization of a Trypsin-Like Protease From the Bacterium Bacteroides Gingivalis Isolated From Human Dental Plaque," *Archs. Oral. Biol.*, vol. 29, No. 7, pp. 559-564, 1984.
Albandar et al., Destructive periodontal disease in adults 30 years of age and older in the United States, 1988-1994, Journal of Periodontology, vol. 70, pp. 13-29, 1999.
Alm et al., The MicrobesOnline Web site for comparative genomics, Genome Research, vol. 15, pp. 1015-1022, 2005.
Bramanti et al. Roles of porphyrins and host iron transport proteins in regulation of growth of *Porphyromonas gingivalis* W50, Journal of Bacteriology, vol. 173, pp. 7330-7339, 1991.
Brochu et al., Acquisition of iron from human transferrin by *Porphyromonas gingivalis*: a role for Arg- and Lys-gingipain activities, Oral Microbiology and Immunology, vol. 16, pp. 79-87, 2001.
Capestany et al., Role of the *Poiphyromonas gingivalis* InlJ Protein in Homotypic and Heterotypic Biofilm Development, Infection and Immunity, vol. 74, pp. 3002-3005, 2006.
Carter et al., Humanization of an Anti-p185HER2 Antibody for Human Cancer Therapy, Proceedings of the National Academy of Science USA, vol. 89, pp. 4285-4289, 1989.
Chen et al., *Porphyromonas gingivalis* gingipains and adhesion to epithelial cells, Infection and Immunity, vol. 69, pp. 3048-3056, 2001.
Cossart et al, Bacterial invasion: the paradigms of enteroinvasive pathogens, Science, vol. 304, pp. 242-248, 2004.
Curtiss et al., A virulent *Salmonella typhimurium* Acya Acrp oral vaccine strains expressing a streptococcal colonization and virulence antigen, Vaccine, vol. 6, pp. 155-160, 1988.
Dashper et al., Characterization of a novel outer membrane herninbinding protein of *Porphyromonas gingivalis*, Journal of Bacteriololgy., vol. 182, pp. 6456-6462, 2000.
Dashper et al., Sodium ion-driven serine/threonine transport in *Porphyromonas gingivalis*, Journal of Bacteriology, vol. 183, pp. 4142-4148, 2001.

(56) References Cited

OTHER PUBLICATIONS

Dashper et al., Hemoglobin hydrolysis and haem acquisition by *Porphyromonas gingivalis*, Oral Microbiology and Immunology, vol. 9, pp. 50-56, 2004.
Dashper et al., A novel *Porphyromonas gingivalis* FeoB plays a role in manganese accumulation, The Journal of Biological Chemistry, vol. 280, pp. 28095-28102, 2005.
Database Ref. Seq, Accession Nos. NC_002950.2 and N13_904903, Jan. 12, 2009.
Devereaux et al., A comprehensive set of sequence analysis programs for the VAX, Nucleic Acids Research, vol. 12, pp. 387-395, 1984.
Diaz et al., The effect of oxygen on the growth and physiology of *Porphyromonas gingivalis*, Oral Microbiology and Immunology, vol. 19, pp. 88-94, 2004.
Diaz et al., Role of oxyR in the oral anaerobe *Porphyromonas gingivalis*, Journal of Bacteriology, vol. 188, pp. 2454-2462, 2006.
Dramsi et al., Entry of *Listeria monocytogenes* into hepatoeytes requires expression of in inlB, a surface protein of the internalin multigene family, Molecular Microbiology, vol. 16, pp. 251-261, 1995.
Duran-Pinedo et al., The RprY response regulator of *Porphyromonas gingivalis*, Molecular Microbiology, vol. 64, pp. 1416, 2007.
Eymann et al., A comprehensive proteome map of growing *Bacillus subtilis* cells, Proteomics, vol. 4, pp. 2849-2876, 2004.
Fletcher et al., Virulence of a *Porphyramonas gingivalis* W83 mutant defective in the prtH gene, Infection and Immunity, vol. 63, pp. 1521-1528, 1995.
Genco et al., Characterization of a Tn4351-generated hemin uptake mutant of *Porphyramonas gingivalis*: evidence for the coordinate regulation of virulence factors by hemin, Infection and Immunity, vol. 63, pp. 2459-2466, 1995.
Guina et al., Quantitative proteomic analysis indicates increased synthesis of a quinolone by *Pseudomonas aeruginosa* isolates from cystic fibrosis airways, Proceedings of the National Academy of Science USA, vol. 100, pp. 2771-2776, 2003.
Haffajee et al., Microbial etiological agents of destructive periodontal diseases, Periodontology 2000, vol. 5, pp. 78-111, 1994.
Huse et al., Generation of a large combinatorial library of the immunoglobulin repertoire in phage lambda, Science, vol. 246, pp. 1275-1281, 1989.
Jones et al., Replacing the complementarity-determining regions in a human antibody with those from a mouse, Nature, vol. 321, pp. 522-525, 1986.
Lamont et al, Interaction of *Porphyromonas gingivalis* with gingival epithelial cells maintained in culture, Oral Microbiology and Immunology, vol. 7, pp. 364-367, 1992.
Lamont et al., *Porphyromonas gingivalis* invasion of gingival epithelial cells, Infection and Immunity, vol. 63, pp. 3878-3885, 1995.
Li et al., Protein profiling with cleavable isotope-coded affinity tag (cICAT) reagents: the yeast salinity stress response, Molecular and Cellular Proteomics, vol. 2, pp. 1198-1204, 2003.
Marino et al., A framework for interpreting the leucine-rich repeats of the Listeria internalins, Proceedings of the National Academy of Science USA, vol. 97, pp. 8784-8788, 2000.
McKee et al., Effect of hemin on the physiology and virulence of *Bacteroides gingivalis* W50, Infection and Immunology, vol. 52, pp. 349-355, 1986.
Moore et al., The bacteria of periodontal diseases, Periodontology 2000, vol. 5, pp. 66-77, 1994.
Needleman et al., A general method applicable to the search for similarities in the amino acid sequence of two proteins, Journal of Molecular Biology, vol. 48, pp. 443-453, 1970.
Nelson et al., "Complete Genome Sequence of the Oral Pathogenic Bacterium *Porphyromonas gingivalis* strain W83," Journal of Bacteriology, vol. 185, No. 18, pp. 5591-5601, Sep. 2003.
Okano et al., Proteomics-based analysis of a counter-oxidative stress system in *Porphyromonas gingivalis*, Proteomics, vol. 6, pp. 251-258, 2006.

Park et al., Identification of *Porphyromonas gingivalis* genes specifically expressed in human gingival epithelial cells by using differential display reverse transcription-PCR, Infection and Immunity, vol. 72, pp. 3752-3758, 2004.
Pathirana et al., Flow cytometric analysis of adherence of *Porphyromonas gingivalis* to oral epithelial cells, Infection and Immunity, vol. 75, pp. 2484-2492, 2007.
Peng et al., Evaluation of multidimensional chromatography coupled with tandem mass spectrometry (LC/LC-MS/MS) for large-scale protein analysis: the yeast proteome, Journal of Proteome Research, vol. 2, pp. 43-50, 2003.
Price et al., A novel method for accurate operon predictions in all sequenced prokaryotes, Nucleic Acids Research, vol. 33, pp. 880-892, 2005.
Reichman et al., Reshaping human antibodies for therapy, Natu e, vol. 332, pp. 323-327, 1988.
Ross et al., Identification of vaccine candidate antigens from a genomic analysis of *Porphyromonas gingivalis*, Vaccine, vol. 19, pp. 4135-4142, 2001.
Sabet et al., LPXTG protein InlJ, a newly identified internalin involved in *Listeria monocytogenes* virulence, Infection and Immunity, vol. 73, pp. 6912-6922, 2005.
Schifferle et al., Effect of protoporphyrin DC limitation on *Porphyromonas gingivalis*, Journal of Endodonics, vol. 22, pp. 352-355, 1996.
Schramm et al., Nucleotide sequence of the colicin B activity gene cba: consensus pentapeptide among TonB-dependent colicins and receptors, Journal of Bacteriology, vol. 169, pp. 3350-3357, 1987.
Schubert et al., Structure of internalin, a major invasion protein of *Listeria monocytogenes*, in complex with its human receptor E-cadherin, Cell, vol. 111, pp. 825-836, 2002.
Seers et al, The RgpB C-terminal domain has a role in attachment of RgpB to the outer membrane and belongs to a novel C-terminal-domain family found in *Porphyromonas gingivalis*, Journal of Bacteriology, vol. 188, pp. 6376-6386, 2006.
Shah et al., The porphyrin pigmentation of subspecies of *Bacteroides melaninogenicus*, Biochemical Journal, vol. 180, pp. 45-50, 1979.
Sharp et al., The codon Adaptation Index—a measure of directional synonymous codon usage bias, and its potential applications, Nucleic Acids Research, vol. 15, pp. 1281-1295, 1987.
Shi et al., Genetic analyses of proteolysis, hemoglobin binding, and hemagglutination of *Porphyromonas gingivalis*. Construction of mutants with a combination of rgpA, rgpl3, kgp, and hagA, The Journal of Biological Chemistry, vol. 274, pp. 17955-17604, 1999.
Shizukuishi et al., Effect of concentration of compounds containing iron on the growth of *Porphyromonas gingivalis*, FEMS Microbiology Letters, vol. 131, pp. 313-317, 1995.
Simpson et al., Characterization and expression of HmuR, a Tonl3-dependent hemoglobin receptor of *Porphyromonas gingivalis*, Journal of Bacteriology, vol. 182, pp. 5737-5748, 2000.
Smalley et al. Hacinin-binding proteins of *Porphyromonas gingivalis* W50 grown in a chemostat under haemin-1 imitation. Journal of General Microbiology, 1993, vol. 139, pp. 2145-2150.
Smalley et al., The periodontopathogen *Porphyromonas gingivalis* binds iron protoporphyrin IX in the mu-oxo dimeric form: an oxidative buffer and possible pathogenic mechanism, Biochemical Journal, vol. 331 (Pt3), pp. 681-685, 1998.
Smalley et al., The periodontal pathogen *Porphyromonas gingivalis* harnesses the chemistry of the mu-oxo bishaem of iron protoporphyrin IX to protect against hydrogen peroxide, FEMS Microbiology Letters, vol. 183, pp. 159-164, 2000.
Supek et al., INCA: synonymous codon usage analysis and clustering by means of self-organizing map, Bioinformatics, vol. 20, pp. 2329-2330, 2004.
Thompson et al., CLUSTAL W: improving the sensitivity of progressive multiple sequence alignment through sequence weighting, position-specific gap penalties and weight matrix choice, Nucleic Acids Research, vol. 22, pp. 4673-4680, 1994.
Tribble et al., A *Porphyromonas gingivalis* haloacid dehalogenase family phosphatase interacts with human phosphoproteins and is important for invasion, Proceedings of the National Academy of Science USA, vol. 103, pp. 11027-11032, 2006.

(56) References Cited

OTHER PUBLICATIONS

Veith et al., Identification of a novel heterodimeric outer membrane protein of *Porphyromonas gingivalis* by two-dimensional gel electrophoresis and peptide mass fingerprinting, European Journal of Biochemistry, vol. 268, pp. 4748-4757, 2001.

Wang et al., An analysis of the proteomic profile for Thermoanaerobacter tengcongensis under optimal culture conditions, Proteomics, vol. 4, pp. 136-150, 2004.

Washburn et al., Large-scale analysis of the yeast proteome by multidimensional protein identification technology, Nature Biotechnology, vol. 19, pp. 242-247, 2001.

Yu et al., Predicting subcellular localization of proteins for Gram-negative bacteria by support vector machines based on n-peptide compositions, Protein Science, vol. 13, pp. 1402-1406, 2004.

Zhang et al., Differential protein expression by *Porphyromonas gingivalis* in response to secreted epithelial cell components, Proteomics, vol. 5, pp. 198-211, 2005.

Houghten et al., "Relative Importance of Position and Individual Amino Acid Residues in Peptide Antigen-Antibody Interactions: Implications in the Mechanism of Antigenic Drift and Antigenic Shift Vaccines," 1986, Fred Brown, Ed.

Lederman et al., "A Single Amino Acid Substitution in a Common African Allele of the CD4 Molecule Ablates Binding of the Monoclonal Antibody, OKT4," Molecular Immunology, vol. 28, pp. 1171-1181, 1991.

Li et al., "β-Endorphin omission analogs: Disssociation of immunoreactivity from other biological activities," Proc. Natl. Acad. Sci. USA, vol. 77, pp. 3211-3214, 1980.

Campbell, "Assay Techniques," Monoclonal Antibody Technology, Chapter 2, 1986.

Bohgal et al., "A cell-associated protein complex of *Porphyromonas gingivalis* W50 composed of Arg- and Lys-specific cysteine proteinases and adhesins," Microbiology, vol. 143, pp. 2485-2495, 1997.

O'Brien-Simpson et al., "RgpA-Kgp Peptide-Based Immunogens Provide Protection Against *Porphyromonas gingivalis* Challenge in Murine Lesion Model," Infection and Immunity, 68(7): 4055-4063, 2000.

Hu et al., "Coptidis rhizome inhibits growth and proteases of oral bacteria," Oral Diseases, vol. 6, No. 5, pp. 297-302, Sep. 1, 2000.

Dashper et al., "Inhibition of *Porphyromonas gingivalis* biofilm by oxante," Antimicrobial Agents and Chemotherapy, vol. 54, No. 3, pp. 1311-1314, Mar. 1, 2010.

Seffernick et al., "Melamine Deaminase and Atrazine Chlorhydrolase: 98 Percent Identical but Functionally Different," Journal of Bacteriology, vol. 183, No. 8, pp. 2405-2410, Apr. 2001.

Witkowski et al., "Conversion of a β-Ketoacyl Synthase to a Malonyl Decarboxylase by Replacement of the Active-Site Cysteine with Glutamine," vol. 39, pp. 11643-11650, 1999.

Office Action issued on Apr. 3, 2013 in U.S. Appl. No. 13/548,454 (US 2013/0028847).

Office Action issued on Dec. 3, 2013 in U.S. Appl. No. 13/548,454 (US 2013/0028847).

Office Action issued on Feb. 21, 2014 in U.S. Appl. No. 13/623,442 (US 2013/0202641).

Office Action issued on Oct. 7, 2013 in U.S. Appl. No. 13/623,442 (US 2013/0202641).

Office Action issued on Aug. 20, 2013 in U.S. Appl. No. 13/623,442 (US 2013/0202641).

\* cited by examiner

FIGURE 6

SEQ ID NO: 1 - Amino Acid sequence of PG0350

MKRKPLFSALVILSGFFGSVHPASAQKVPAPVDGERIIMELSEADVECTI
KIEAEDGYANDIWADLNGNGKYDSGERLDSGEFRDVEFRQTKAIVYGKMA
KFLFRGSSAGDYGATFIDISNCTGLTAFDCFANLLTELDLSKANGLTFVN
CGKNQLTKLDLPANADIETLNCSKNKITSLNLSTYTKLKELYVGDNGLTA
LDLSANTLLEELVYSNNEVTTINLSANTNLKSLYCINNKMTGLDVAANKE
LKILHCNNNQLTALNLSANTKLTTLSFFNNELTNIDLSDNTALEWLFCNG
NKLTKLDVSANANLIALQCSNNQLTALDLSKTPKLTTLNCYSNRIKDTAM
RALIESLPTITEGEGRFVPYNDDEGGEEENVCTTEHVEMAKAKNWKVLTS
WGEPFPGITALISIEGESEYSVYAQDGILYLSGMEQGLPVQVYTVGGSMM
YSSVASGSAMEIQLPRGAAYVVRIGSHAIKTAMP

FIGURE 7

SEQ ID NO: 2 – Amino Acid sequence of PG1374

MKLSSKKILAIIALLTMGHAVQAQFVPAPTTGIRMSVTTTKAVGEKIELL
VHSIEKKGIWIDLNGDATYQQGEEITVFDEAYHEYTIGTQTLTIYGNTTR
LGCRSTGATAVDVTKNPNLTYLACPKNNLKSLDLTQNPKLLRVWCDSNEI
ESLDLSGNPALIILGCDRNKLTELKTDNNPKLASLWCSDNNLTELELSAN
PRLNDLWCFGNRITKLDLSANPLLVTLWCSDNELSTLDLSKNSDVAYLWC
SSNKLTSLNLSGVKGLSVLVCHSNQIAGEEMTKVVNALPTLSPGAGAQSK
FVVVDLKDTDEKNICTVKDVEKAKSKNWRVFDFNGDSDNMLPYEGSPTSN
LAVDAPTVRIYPNPVGRYALVEIPESLLGQEAALYDMNGVKVYSFAVESL
RQNIDLTHLPDGTYFFRLDNYTTKLIKQ

FIGURE 8

SEQ ID NO: 3 - Amino Acid sequence of PG1019

MKKNFLFFSLVLAAIMSLLSSCAKDTPDAPEQYAITIRAKLPEGSTIESLAGIAIEFLDL
RTQQKVEKQLDKAGVCSLSLDASVYTITIRGEIGNNSIVAIKENYSIAENTTLELPLIVT
KIRPSGLLFKEVFFNGETNNGQMMHPDQYFVIYNNSDKVVYADGVAFGLAAHANVT
GEDAFTEELTKNNRIVLSMIYTIPGNGSQYPIQPGGQLVIAGTAINHHDAEHPNSVDLS
GADLEVYEPDQPANFGQDVDNPNVPNMVKIFNRFGVFMMHPRGFIPPVLFEIDEPIET
FLAKNQFEYTNNDGENIMLYAVPVENVLDGIETANTGNMKVKSLPVTVDKSMIGVP
GCHRGILILRKTEEKNGRTYMIDTNDSENDCIARQGQNSFPARF

FIGURE 9

SEQ ID NO: 4 - Amino Acid sequence of PG0618

MTPILNTVFPEFKLNAYHNGEFKVITNEDLKGKWSLVVFYPGDFTFVCPTELEDLANK
YEEFKQLGVEVYSCSCDTHFVHKAWADASPAIKKVQYPMLADPSGALTRDLGILIDD
VHMAYRGSFVINPEGIIKIVELNDNSVGRDAEEILRKIKAAQYVAAHDGQVCPAKWRE
GQQTLKPSIDLVGKI

PORPHYROMONAS GINGIVALIS POLYPEPTIDES USEFUL IN THE PREVENTION OF PERIODONTAL DISEASE

RELATED APPLICATIONS

This is a division of Ser. No. 12/306,495, filed Dec. 23, 2008, now abandoned. Ser. No. 12/306,495 is a national stage entry of PCT/AU2007/000890, filed Jun. 27, 2007. The application also claims foreign priority to AU 2006903425, filed Jun. 27, 2006.

FIELD OF THE INVENTION

The present invention relates to compositions and methods of isolating *Porphyromonas gingivalis* (*P. gingivalis*) proteins useful in the prevention of and treatment of periodontal disease. More particularly, the invention is directed to vaccine compositions and methods based on *P. gingivalis* proteins identified to be regulated by haem availability that can be used in the prevention and treatment of periodontal disease.

BACKGROUND OF THE INVENTION

Periodontal disease is a chronic bacterial infection that affects the gums and bone supporting the teeth. Periodontal disease begins when the bacteria in plaque (the sticky biofilm that constantly forms on teeth) causes the gums to become inflamed. Periodontal disease can affect the gingival tissue (gums); periodontal membrane (connective tissue embedded in the cementum and alveolar bone); cementum (mineralized connective tissue covering the roots of the teeth); and the alveolar bone (bone socket). Depending on the progression of the disease, there may occur a destruction of periodontal membranes, alveolar bone loss, and apical migration of the connective tissue attachment. Advanced periodontal disease may result in the formation of periodontal pockets harbouring bacterial plaque, and progressive loosening and eventual loss of teeth. Periodontal disease includes gingivitis that can advance to periodontitis. Chronic periodontitis is an inflammatory disease of the supporting tissues of teeth that is associated with specific bacteria in subgingival dental plaque. The disease has been estimated to affect around 35% of dentate adults and is a major cause of tooth loss in the Western world[1]. *P. gingivalis*, a member of the normal oral microflora of subgingival dental plague, has been implicated as one of the major opportunistic pathogens in the progression of this disease[2].

*P. gingivalis* is a black-pigmented, asaccharolytic, Gram-negative anaerobic, cocco-bacillus, that relies on the fermentation of amino acids for energy production[3]. Like most bacteria, *P. gingivalis* has an essential growth requirement for iron that it preferentially acquires in the form of haem, a molecule comprised of a protoporphyrin IX ring (PPIX) with a co-ordinated central ferrous atom[4]. This utilization of haem as an iron source may reflect the inability of *P. gingivalis* to synthesize PPIX de novo[5]. Haem is preferentially obtained from haemoglobin, and is acquired through the activity of the cell-surface Arg- and Lys-specific proteinase/adhesin complex[4,6,7], possibly in conjunction with a TonB-linked outer membrane receptor, HmuR[5]. Unlike aerobic or facultative bacteria that obtain iron using siderophores *P. gingivalis* does not produce siderophores and lacks the ferric reductase activity usually associated with siderophore-mediated iron acquisition[9,10]. *P. gingivalis* stores haem on its surface in the form of μ-oxo bis-haem, which has inherent catalase activity that helps to protect the cell from oxidative attack[11]. For *P. gingivalis* to be able to compete with the large numbers and diversity of bacteria within the micronutrient-limiting environment of the oral cavity[12] it not only has to establish itself but also has to evade or overcome numerous host defences.

The initiation and progression of periodontal disease is associated with bleeding at the site of disease, thereby providing an elevated level of haemoglobin. Therefore in order to help understand the mechanism by which *P. gingivalis* establishes and proliferates in subgingival plaque and initiates disease it is important to determine the changes in relative protein abundances of *P. gingivalis* during the transition from micronutrient poor (haem-limitation) to rich (haem-excess) conditions.

Although many proteins have been associated with growth under haem-limitation[9,10], no extensive work on the *P. gingivalis* proteome or the changes to the proteome during haem-limitation has been reported.

In developing compositions which would be useful in the prevention and treatment of periodontal disease it is desirable to identify agents that interfere and prevent the initial stages of the disease process.

The present inventors have now developed methods for identifying specific *P. gingivalis* proteins regulated by haem availability that can be used as suitable targets for the prevention and treatment of periodontal disease.

SUMMARY OF THE INVENTION

The present inventors have successfully developed methods of identifying *P. gingivalis* proteins regulated by haem availability that are responsible for *P. gingivalis* metabolism, virulence and invasion of host cells. In particular, two specific internalin-like *P. gingivalis* proteins, namely PG0350, PG1374 involved in the internalization of *P. gingivalis* by host cells, a hypothetical protein, PG1019 purported to be a cell surface lipoprotein and an alkyl hydroperoxide reductase protein, PG0618 have been identified as useful targets for the prevention and treatment of periodontal disease.

A first aspect of the invention is an isolated antigenic *P. gingivalis* polypeptide, the polypeptide being selected from the group consisting of:
  (i) the PG0350 protein having the amino acid sequence of SEQ ID NO:1;
  (ii) the PG1374 protein having the amino acid sequence of SEQ ID NO:2;
  (iii) the PG1019 protein having the amino acid sequence of SEQ ID NO:3;
  (iv) the PG0618 protein having the amino acid sequence of SEQ ID NO:4;
  (v) an amino acid sequence at least 85% identical to the amino acid sequence of SEQ ID NO:1 or SEQ ID NO:2 or SEQ ID NO:3 or SEQ ID NO:4; or
  (vi) an amino acid sequence comprising at least 10 amino acids identical to a contiguous amino acid sequence of SEQ ID NO:1 or SEQ ID NO:2 or SEQ ID NO:3 or SEQ ID NO:4.

A second aspect of the invention is a vaccine composition for use in raising an immune response directed against *P. gingivalis* in a subject, the composition comprising an effective amount of at least one polypeptide of the first aspect of the invention and a pharmaceutically acceptable carrier.

A third aspect of the invention is a method of preventing or treating a subject for periodontal disease comprising administering to the subject a vaccine composition according to the present invention.

A fourth aspect of the invention is an antibody raised against a polypeptide of the first aspect of the present invention. Preferably, the antibody binds specifically to the polypeptides of the present invention.

A fifth aspect of the invention is a composition useful in the prevention or treatment of periodontal disease, the composition comprising an antibody of the fourth aspect of the present invention and a pharmaceutically acceptable carrier.

In a sixth aspect of the present invention there is provided a method of identifying a *P. gingivalis* polypeptide involved in the progression of periodontal disease, wherein the method comprises the steps of:
a) determining the relative amount of a polypeptide or peptide thereof produced by *P. gingivalis* grown under haem limited conditions; and
b) determining the relative amount of the polypeptide or peptide thereof produced by *P. gingivalis* grown under higher haem conditions than step a);
wherein an increase in the amount of the polypeptide or peptide fragment thereof detected in step a) compared to step b) indicates that the polypeptide is involved in the progression of periodontal disease.

In a seventh aspect of the present invention there is provided an interfering RNA molecule, the molecule comprising a double stranded region of at least 19 base pairs in each strand wherein one of the strands of the double stranded region is complementary to a region of SEQ ID NO: 5 or SEQ ID NO: 6 or SEQ ID NO: 7 or SEQ ID NO: 8.

In an eighth aspect of the present invention there is provided for the use of at least one polypeptide of the first aspect of the present invention in the manufacture of a medicament for the treatment of periodontal disease in a subject.

BRIEF DESCRIPTION OF THE FIGURES

FIG. 6 shows the amino acid sequence of PG0350 protein (referred to as SEQ ID NO:1 as also indicated in the sequence listing).

FIG. 7 shows the amino acid sequence of PG1374 protein (referred to as SEQ ID NO:2 as also indicated in the sequence listing).

FIG. 8 shows the amino acid sequence of PG1019 protein (referred to as SEQ ID NO:3 as also indicated in the sequence listing).

FIG. 9 shows the amino acid sequence of PG0618 protein (referred to as SEQ ID NO:4 as also indicated in the sequence listing).

DETAILED DESCRIPTION OF THE INVENTION

Figure 1:
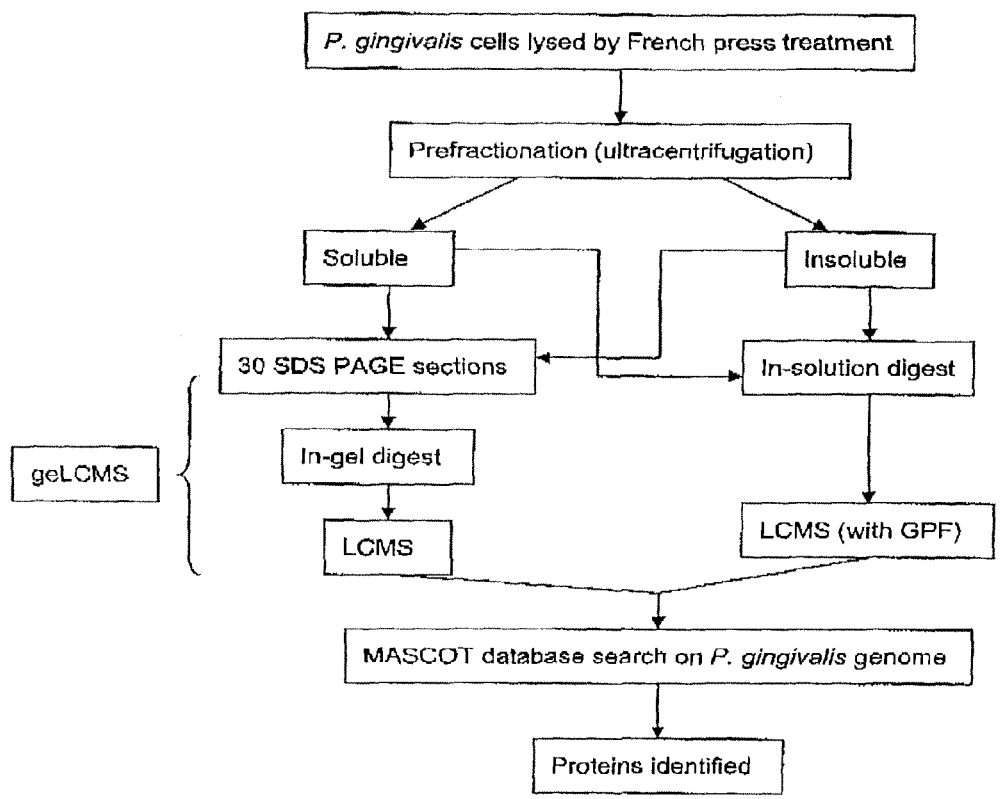
FIG. 1 shows a diagrammatic representation of the combined strategy used to identify proteins from *P. gingivalis* grown under haem-limitation. The lysed cells were prefractionated into soluble and insoluble fractions using ultra-centrifugation, followed by analysis of these two fractions. The separation and analysis procedure consists of two main methods; LCMS with gas phase fractionation and geLCMS.

The present invention advantageously provides the identification of *P. gingivalis* proteins regulated by haem availability as useful targets for the prevention and treatment of periodontal disease. Preferably, the invention provides the identification of *P. gingivalis* proteins upregulated by hacm-limitation as useful targets for the prevention and treatment of periodontal disease.

In particular, the invention provides an isolated antigenic *P. gingivalis* polypeptide, the polypeptide being selected from the group consisting of:
(i) the PG0350 protein having the amino acid sequence of SEQ ID NO:1;
(ii) the PG1374 protein having the amino acid sequence of SEQ ID NO:2;
(iii) the PG1019 protein having the amino acid sequence of SEQ ID NO:3;
(iv) the PG0618 protein having the amino acid sequence of SEQ ID NO:4;
(v) an amino acid sequence at least 85% identical to the amino acid sequence of SEQ ID NO:1 or SEQ ID NO:2 or SEQ ID NO:3 or SEQ ID NO:4; or
(vi) an amino acid sequence comprising at least 10 amino acids identical to a contiguous amino acid sequence of SEQ ID NO:1 or SEQ ID NO:2 or SEQ ID NO:3 or SEQ ID NO:4.

Preferably, the isolated antigenic polypeptide is 90%, 95%, 96%, 97%, 98%, 99% or 100% identical to the amino acid sequence of SEQ ID NO:1 or SEQ ID NO:2 or SEQ ID NO:3 or SEQ ID NO:4.

Preferably, the isolated antigenic polypeptide comprises an amino acid sequence comprising at least 20, 30, 40, 50, 60, 70, 80, 90 or 100 amino acids identical to a contiguous amino acid sequence of SEQ ID NO:1 or SEQ ID NO:2 or SEQ ID NO:3 or SEQ ID NO:4.

In a preferred embodiment, the antigenic polypeptides comprise amino acid sequences that compose the hydrophilic, surface-exposed regions of the PG1374 or PG0350 or PG1019 or PG0618 protein.

The terms "peptides, proteins, and polypeptides" are used interchangeably herein. The polypeptides of the present invention can include recombinant polypeptides such as fusion polypeptides. Methods for the production of a fusion polypeptide are well-known to those skilled in the art.

As will be well understood by those skilled in the art alterations may be made to the amino acid sequences set out in the Sequence Listings. These alterations may be deletions, insertions, or substitutions of amino acid residues. The altered polypeptides can be either naturally occurring (that is to say, purified or isolated from a natural source) or synthetic (for example, by site-directed metagenesis on the encoding DNA). It is intended that such altered polypeptides which have at least 85%, preferably at least 90%, 95%, 96%, 97%, 98% or 99% identity with the sequences set out in the Sequence Listing are within the scope of the present invention. Antibodies raised against these altered polypeptides will also bind to the polypeptides having one of the sequences set out in the Sequence Listings.

Whilst the concept of conservative substitution is well understood by the person skilled in the art, for the sake of clarity conservative substitutions are those set out below.

Gly, Ala, Val, Ile, Leu, Met;
Asp, Glu, Ser;
Asn, Gln;
Ser, Thr;
Lys, Arg, His;
Phe, Tyr, Trp, His; and
Pro, Nα-alkalamino acids.

The practice of the invention will employ, unless otherwise indicated, conventional techniques of chemistry, molecular biology, microbiology, recombinant DNA, and immunology well known to those skilled in the art. Such techniques are described and explained throughout the literature in sources such as, Perbal, A Practical Guide to Molecular Cloning, John Wiley and Sons (1984)[15], Sambrook et al., Molecular Cloning: A Laboratory Manual, Cold Spring Harbour Laboratory Press (1989)[16], Brown (editor). Essential Molecular Biology: A Practical Approach, Volumes 1 and 2, IRL Press (1991)[17], Glover & Hames (editors), DNA Cloning: A Practical Approach, Volumes 1-4, IRL Press (1995 and 1996)[18], and Ausubel cc al., (Editors), Current Protocols in Molecular Biology, Greene Pub. Associates and Wiley-Interscience (1988, including all updates until present)[19]. The disclosure of these texts are incorporated herein by reference.

An "isolated polypeptide" as used herein refers to a polypeptide that has been separated from other proteins, lipids, and nucleic acids with which it naturally occurs or the polypeptide or peptide may be synthetically synthesised. Preferably, the polypeptide is also separated from substances, for example, antibodies or gel matrix, for example, polyacrylamide, which are used to purify it. Preferably, the polypeptide constitutes at least 10%, 20%, 50%, 70%, and 80% of dry weight of the purified preparation. Preferably, the preparation contains a sufficient amount of polypeptide to allow for protein sequencing (i.e. at least 1, 10, or 100 mg).

The isolated polypeptides described herein may be purified by standard techniques, such as column chromatography (using various matrices which interact with the protein products, such as ion exchange matrices, hydrophobic matrices and the like), affinity chromatography utilizing antibodies specific for the protein or other ligands which bind to the protein.

An "antigenic polypeptide" used herein is a moiety, such as a polypeptide, analog or fragment thereof, that is capable of binding to a specific antibody with sufficiently high affinity to form a detectable antigen-antibody complex. Preferably, the antigenic polypeptide comprises an immunogenic component that is capable of eliciting a humoral and/or cellular immune response in a host animal.

A "contiguous amino acid sequence" as used herein refers to a continuous stretch of amino acids.

In determining whether or not two amino acid sequences fall within a specified percentage limit, those skilled in the art will be aware that it is necessary to conduct a side-by-side comparison or multiple alignments of sequences. In such comparisons or alignments, differences will arise in the positioning of non-identical residues, depending upon the algorithm used to perform the alignment. In the present context, reference to a percentage identity or similarity between two or more amino acid sequences shall be taken to refer to the number of identical and similar residues respectively, between said sequences as determined using any standard algorithm known to those skilled in the art. For example, amino acid sequence identities or similarities may be calculated using the GAP programme and/or aligned using the PILEUP programme of the Computer Genetics Group, Inc., University Research Park, Madison, Wis., United States of America[20]. The GAP programme utilizes the algorithm of Needleman and Wunsch[21] to maximise the number of identical/similar residues and to minimise the number and length of sequence gaps in the alignment. Alternatively or in addition, wherein more than two amino acid sequences are being compared, the Clustal W programme[22] is used.

The present invention also provides a vaccine composition for use in raising an immune response directed against P. gingivalis in a subject, the composition comprising an effective amount of at least one polypeptide of the first aspect of the invention and a pharmaceutically acceptable carrier.

The vaccine composition of the present invention preferably comprises an antigenic polypeptide that comprises at least one antigen that can be used to confer immunity against P. gingivalis. The subject treated by the method of the invention may be selected from, but is not limited to, the group consisting of humans, sheep, cattle, horses, bovine, pigs, poultry, dogs and cats. Preferably, the subject is a human. An immune response directed against P. gingivalis is achieved in a subject, when the subject's immune system produces antibodies against the specific antigenic polypeptides.

The vaccine composition is preferably administered to a subject to induce immunity to P. gingivalis and thereby prevent periodontal disease. The term "effective amount" as used herein means a dose sufficient to elicit an immune response against P. gingivalis. This will vary depending on the subject and the level of P. gingivalis infection and ultimately will be decided by the attending scientist, physician or veterinarian.

The vaccine composition of the present invention comprises a suitable pharmaceutically-acceptable carrier, such as diluent and/or adjuvant suitable for administration to a human or animal subject. The vaccine preferably comprises a suitable adjuvant for delivery orally by nasal spray, or by injection to produce a specific immune response against P. gingivalis. A vaccine of the present invention can also be based upon a recombinant nucleic acid sequence encoding an antigenic polypeptide of the present invention, wherein the nucleic acid sequence is incorporated into an appropriate vector and expressed in a suitable transformed host (e.g. E. coli, Bacillus subtilis, Saccharomyces cerevisiae, COS cells, CHO cells and HeLa cells) containing the vector. The vaccine can be produced using recombinant DNA methods as illustrated herein, or can be synthesized chemically from the amino acid sequence described in the present invention. Additionally, according to the present invention, the antigenic polypeptides may be used to generate P. gingivalis antisera useful for passive immunization against periodontal disease and infections caused by P. gingivalis.

Various adjuvants known those skilled in the art are commonly used in conjunction with vaccine formulations. The adjuvants aid by modulating the immune response and in attaining a more durable and higher level of immunity using smaller amounts of vaccine antigen or fewer doses than if the vaccine antigen were administered alone. Examples of adjuvants include incomplete Freunds adjuvant (IFA), Adjuvant 65 (containing peanut oil, mannide monooleate and aluminium monostrearate), oil emulsions, Ribi adjuvant, the pluronic polyols, polyamines, Avridine, Quil A, saponin, MPL, QS-21, and mineral gels such as aluminium salts. Other examples include oil in water emulsions such as SAF-1, SAF-0, MF59, Seppic ISA720, and other particulate adjuvants such as ISCOMs and ISCOM matrix. An extensive but exhaustive list of other examples of adjuvants are listed in Cox and Coulter 1992[23]. In addition to the adjuvant the vaccine may include conventional pharmaceutically acceptable carriers, excipients, fillers, buffers or diluents as appropriate. One or more doses of the vaccine containing adjuvant may be administered prophylactically to prevent periodontal disease or therapeutically to treat already present periodontal disease.

In another preferred vaccine composition the preparation is combined with a mucosal adjuvant and administered via the oral or nasal route. Examples of mucosal adjuvants are cholera toxin and heat labile *E. coli* toxin, the non-toxic B subunits of these toxins, genetic mutants of these toxins which have reduced toxicity. Other methods which may be utilised to deliver the antigenic polypeptides orally or nasally include incorporation of the polypeptides into particles of biodegradable polymers (such as acrylates or polyesters) by microencapsulation to aid uptake of the microspheres from the gastrointestinal tract or nasal cavity and to protect degradation of the proteins. Liposomes, ISCOMs, hydrogels are examples of other potential methods which may be further enhanced by the incorporation of targeting molecules such as LTB, CTB or lectins (mannan, chitin, and chitosan) for delivery of the antigenic polypeptides to the mucosal immune system. In addition to the vaccine and the mucosal adjuvant or delivery system the vaccine may include conventional pharmaceutically acceptable carriers, excipients, fillers, coatings, dispersion media, antibacterial and antifungal agents, buffers or diluents as appropriate.

Another mode of this embodiment provides for either, a live recombinant viral vaccine, recombinant bacterial vaccine, recombinant attenuated bacterial vaccine, or an inactivated recombinant viral vaccine which is used to protect against infections caused by *P. gingivalis*. Vaccinia virus is the best known example, in the art, of an infectious virus that is engineered to express vaccine antigens derived from other organisms. The recombinant live vaccinia virus, which is attenuated or otherwise treated so that it does not caused disease by itself, is used to immunise the host. Subsequent replication of the recombinant virus within the host provides a continual stimulation of the immune system with the vaccine antigens such as the antigenic polypeptides, thereby providing long lasting immunity.

Other live vaccine vectors include: adenovirus, cytomegalovirus, and preferably the poxviruses such as vaccinia[24] and attenuated *salmonella* strains[25-28]. Live vaccines are particularly advantageous because they continually stimulate the immune system which can confer substantially long-lasting immunity. When the immune response is protective against subsequent *P. gingivalis* infection, the live vaccine itself may be used in a protective vaccine against *P. gingivalis*. In particular, the live vaccine can be based on a bacterium that is a commensal inhabitant of the oral cavity. This bacterium can be transformed with a vector carrying a recombinant inactivated polypeptide and then used to colonise the oral cavity, in particular the oral mucosa. Once colonised the oral mucosa, the expression of the recombinant protein will stimulate the mucosal associated lymphoid tissue to produce neutralising antibodies. For example, using molecular biological techniques the genes encoding the polypeptides may be inserted into the vaccinia virus genomic DNA at a site which allows for expression of epitopes but does not negatively affect the growth or replication of the vaccinia virus vector. The resultant recombinant virus can be used as the immunogen in a vaccine formulation. The same methods can be used to construct an inactivated recombinant viral vaccine formulation except the recombinant virus is inactivated, such as by chemical means known in the art, prior to use as an immunogen and without substantially affecting the immunogenicity of the expressed immunogen.

As an alternative to active immunisation, immunisation may be passive, i.e. immunisation comprising administration of purified immunoglobulin containing an antibody against a polypeptide of the present invention.

The antigenic polypeptides used in the methods and compositions of the present invention may be combined with suitable excipients, such as emulsifiers, surfactants, stabilisers, dyes, penetration enhancers, anti-oxidants, water, salt solutions, alcohols, polyethylene glycols, gelatine, lactose, magnesium sterate and silicic acid. The antigenic polypeptides are preferably formulated as a sterile aqueous solution. The vaccine compositions of the present invention may be used to complement existing treatments for periodontal disease.

A third aspect of the invention is a method of preventing or treating a subject for periodontal disease comprising administering to the subject a vaccine composition according to the present invention.

In the present method a subject is treated including prophylactic treatment for periodontal disease. Periodontal diseases range from simple gum inflammation to serious disease that results in major damage to the soft tissue and bone that support the teeth. Periodontal disease includes gingivitis and periodontitis. Bacteria, mainly Gram-negative species including *P. gingivalis* cause inflammation of the gums that is called "gingivitis." In gingivitis, the gums become red, swollen and can bleed easily. When gingivitis is not treated, it can advance to "periodontitis" (which means "inflammation around the tooth."). In periodontitis, gums pull away from the teeth and form "pockets" that are infected. The body's immune system fights the bacteria as the plaque spreads and grows below the gum line. If not treated, the bones, gums, and connective tissue that support the teeth are destroyed. The teeth may eventually become loose and have to be removed.

A fourth aspect of the invention is an antibody raised against a polypeptide of the first aspect of the present invention. Preferably, the antibody is specifically directed against the polypeptides of the present invention.

In the present specification the term "antibody" is used in the broadest sense and specifically covers monoclonal antibodies, polyclonal antibodies, multispecific antibodies (e.g., bispecific antibodies), chimeric antibodies, diabodies, triabodies and antibody fragments. The antibodies of the present invention are preferably able to specifically bind to an antigenic polypeptide as hereinbefore described without cross-reacting with antigens of other polypeptides.

The term "binds specifically to" as used herein, is intended to refer to the binding of an antigen by an immunoglobulin variable region of an antibody with a dissociation constant (Kd) of 1 µM or lower as measured by surface plasmon resonance analysis using, for example a BIAcore™ surface plasmon resonance system and BIAcore™ kinetic evaluation software (eg. version 2.1). The affinity or dissociation constant (Kd) for a specific binding interaction is preferably about 500 nM to about 50 pM, more preferably about 500 nM or lower, more preferably about 300 nM or lower and preferably at least about 300 nM to about 50 pM, about 200 nM to about 50 pM, and more preferably at least about 100 nM to about 50 pM, about 75 nM to about 50 pM, about 10 nM to about 50 pM.

It has been shown that the antigen-binding function of an antibody can be performed by fragments of a full length antibody. Examples of binding fragments of an antibody include (1) a Fab fragment, a monovalent fragment consisting of the VL, VH, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody; (v) a dAb fragment which consists of a VH domain, or a VL domain; and (vi) an isolated complementarity determining region (CDR). Furthermore, although the two domains of the Fv fragment, VL and VH, are coded by separate genes, they can be joined, using recombinant methods, by a synthetic linker that enables them to be made as a single protein chain in which the VL and VH regions pair to form monovalent molecules (known as single chain Fv (scFv). Other forms of single chain antibodies, such as diabodies or triabodies are also encompassed. Diabodies are bivalent, bispecific antibodies in which VH and VL domains are expressed on a single polypeptide chain, but using a linker that is too short to allow for pairing between the two domains on the same chain, thereby forcing the domains to pair with complementary domains of another chain and creating two antigen binding sites.

Various procedures known in the art may also be used for the production of the monoclonal and polyclonal antibodies as well as various recombinant and synthetic antibodies which can bind to the antigenic polypeptides of the present invention. In addition, those skilled in the art would be familiar with various adjuvants that can be used to increase the immunological response, depending on the host species, and include, but are not limited to, Freud's (complete and incomplete), mineral gels such as aluminum hydroxide, surface active substances such as lysolecithin, pluronic polyols, polyanions, peptides, oil emulsions, dinitrophenol, and potentially useful human adjuvants such as *Bacillus* Calmette-Guerin (BCG) and *Corynebacterium parvum*. Antibodies and antibody fragments may be produced in large amounts by standard techniques (eg in either tissue culture or serum free using a fermenter) and purified using affinity columns such as protein A (e.g. for murine Mabs), Protein G (eg for rat Mabs) or MEP HYPERCEL (eg for IgM and IgG Mabs).

Recombinant human or humanized versions of monoclonal antibodies are a preferred embodiment for human therapeutic applications. Humanized antibodies may be prepared according to procedures in the literature[29,30]. The recently described "gene conversion metagenesis" strategy for the production of humanized monoclonal antibody may also be employed in the production of humanized antibodies [31]. Alternatively, techniques for generating the recombinant phase library of random combinations of heavy and light regions may be used to prepare recombinant antibodies[32].

The present invention also provides a composition useful in the prevention or treatment of periodontal disease, the composition comprising an antagonist of a *P. gingivalis* polypeptide of the first aspect of the present invention and a pharmaceutically acceptable carrier, wherein the antagonist inhibits *P. gingivalis* infection.

As used herein, the term "antagonist" refers to a nucleic acid, peptide, antibody, ligands or other chemical entity which inhibits the biological activity of the polypeptide of interest. A person skilled in the art would be familiar with techniques of testing and selecting suitable antagonists of a specific protein, such techniques would including binding assays. Possible antagonists of PG0350, PG1374, PG1019 and PG0618 are preferably antibodies, either monoclonal or polyclonal, which will inhibit the binding of these proteins to host cells or other substrates or they may be proteins or peptides that interfere with the binding of these proteins.

The antibodies and antagonists of the present invention have a number of applications, for example, they can be used as antimicrobial preservatives, in oral care products (toothpastes and mouth rinses) for the control of dental plaque and suppression of pathogens associated with dental caries and periodontal diseases. The antibodies and antagonists of the present invention may also be used in pharmaceutical preparations (eg, topical and systemic anti infective medicines).

In a sixth aspect of the present invention there is provided a method of identifying a *P. gingivalis* polypeptide involved in the progression of periodontal disease, wherein the method comprises the steps of:
a) determining the relative amount of a polypeptide or peptide thereof produced by *P. gingivalis* grown under haem limited conditions; and
b) determining the relative amount of the polypeptide or peptide thereof produced by *P. gingivalis* grown under higher haem conditions than step a);
wherein an increase in the amount of the polypeptide or peptide fragment thereof detected in step a) compared to step b) indicates that the polypeptide is involved in the progression of periodontal disease.

In order to grow *P. gingivalis* under haem limited conditions, it is preferred that the concentration of haemin is about 0.1 µg/ml to about 0.5 µg/ml. Haem limiting conditions are achieved when the cell density of the *P. gingivalis* cells is significantly lower than that observed under the growth conditions of step (b) of the method of the invention. The higher haemn conditions of step (b) is preferably achieved using a concentration of haemin of above 5 µg/ml.

A comparison of the relative amounts of a polypeptide in the haem limited and higher haem conditions can be preferably determined by using a differential proteomic approach. Preferably, the amount of a polypeptide is determined by qualitative proteomic analysis commonly used in the art, such as but not limited to, a combined strategy of in-solution and in-gel digestion and LC-MS/MS, analysis using stable isotope labelling strategies (ICAT) in combination with MS.

The isolated antigenic *P. gingivalis* polypeptides identified according to the method defined in the sixth aspect of the invention can be used as targets for treating and preventing periodontal disease. In particular, the isolated polypeptides can be used to develop vaccine compositions against *P. gingivalis*, for instance *P. gingivalis* infection, such as periodontal disease.

The present invention also provides interfering RNA molecules which are targeted against the mRNA molecules encoding the polypeptides of the first aspect of the present invention. Accordingly, in a seventh aspect of the present invention there is provided an interfering RNA molecule, the molecule comprising a double stranded region of at least 19 base pairs in each strand wherein one of the strands of the double stranded region is complementary to a region of SEQ ID NO: 5 or SEQ ID NO: 6 or SEQ ID NO: 7 or SEQ ID NO: 8.

So called RNA interference or RNAi is well known and further information regarding RNAi is provided in Hannon (2002) *Nature* 418: 244-251, and McManus & Sharp (2002) *Nature Reviews: Genetics* 3(10): 737-747, the disclosures of which are incorporated herein by reference.

The present invention also contemplates chemical modification(s) of siRNAs that enhance siRNA stability and support their use in vivo (see for example, Shen et al. (2006) *Gene Therapy* 13: 225-234). These modifications might include inverted abasic moieties at the 5' and 3' end of the sense strand oligonucleotide, and a single phosphorthioate linkage between the last two nucleotides at the 3' end of the antisense strand.

It is preferred that the double stranded region of the interfering RNA comprises at least 20, preferably at least 25, and most preferably at least 30 base pairs in each strand of the double stranded region. The present invention also provides a method of treating a subject for periodontal disease comprising administering to the subject at least one of the interfering RNA molecules of the invention.

In order that the nature of the present invention may be more clearly understood preferred forms thereof will now be described with reference to the following example.

Example 1

1. Materials and Methods 1.1 Bacterial Strain and Chemicals

P. gingivalis W50 (ATCC 53978) was obtained from the culture collection of the Centre for Oral Health Science, The University of Melbourne. Chemicals used were ultra high purity except for MS work where LC MS grade reagents were used (Sigma. Reidel-de Haën).

1.2 Growth and Harvesting of P. gingivalis

P. gingivalis W50 was grown in continuous culture using a Bioflo 110 fermenter/bioreactor (New Brunswick Scientific) with a 400 mL working volume. The growth medium was 37 g/mL brain heart infusion medium (Oxoid) supplemented with 5 mg/mL filter sterilized cysteine hydrochloride, 5.0 μg/mL haemin (haem-excess) or 0.1 μg/mL haemin (haem-limited). Growth was initiated by inoculating the culture vessel with a 24 h batch culture (100 mL) of P. gingivalis grown in the same medium (haem-excess). After 24 h of batch culture growth, the medium reservoir pump was turned on and the medium flow adjusted to give a dilution rate of $0.1\ b^{-1}$ (mean generation time (MGT) of 6.9 h). The temperature of the vessel was maintained at 37° C. and the pH at 7.4±0.1. The culture was continuously gassed with 5% $CO_2$ in 95% $N_2$. Cells were harvested during steady state growth, washed three times with wash buffer (50 mM Tris-HCl pH 8.0, 150 mM NaC, 5 mM $MgCl_2$) at 5000 g for 30 min and disrupted with 3 passes through a French Pressure Cell (SLM, AMINCO) at 138 MPa. The lysed cells were then centrifuged at 2000 g for 30 min to remove unbroken cells followed by ultracentrifugation at 100000 g, producing a soluble (supernatant) and membrane fraction. All fractions were carried out on ice.

1.3 Preparation of Samples for Non-Quantitative Proteome Analysis

Non-quantitative proteome analysis was carried out using two methods, in-solution digestion with trypsin followed by LCMS with gas phase fractionation (GPF) and in-gel digestion followed by LCMS (geLC-MS) as part of a combined strategy (FIG. 1). For the in-solution digestion method, protein was boiled at 95° C. for 3 min, precipitated with TCA (16%) and resuspended in solubilization buffer (8 M Urea, 50 mM Tris-HCl pH 8.3, 5 mM EDTA, 0.05% SDS). Protein concentration was determined with a BCA protein reagent (Pierce) and adjusted to 2 μg/μL. Reduction was carried out with 1 mM DTT for 30 min and alkylation using 10 mM iodoacetamide for 60 min. The solution was diluted with water to a final concentration of 1 M urea before digestion. Digestion was carried out using sequencing-grade modified trypsin (Promega) at a ratio of 1:100 w/w trypsin to protein at 37° C. for 16 h. The digestion was terminated by formic acid addition to a final concentration of 1% v/v. Peptides were then desalted using Sep-Pak C18 cartridges (Waters), dried using a vacuum centrifuge (Thermosavant) and resuspended in 5% acetonitrile in 0.1% TFA. An amount of peptide equivalent to 2 μg was injected for each LC-MS/MS analysis.

For the geLC-MS method, 25 μg of protein was separated on a precast Novex 12% Tris-HCl glycine gel (Invitrogen) and stained overnight with Commassie Brilliant Blue 0-250 (Sigma). The gel was divided into thirty individual sections which were then excised and cut into approximately 1 $mm^3$ cubes. Destaining was carried out three times with a solution of 50% ethanol and 25 mM ammonium bicarbonate (ABC) buffer followed by dehydration with 100% ethanol. Reduction was carried out by incubating the dehydrated gel cubes with 10 mM DTT in 25 mM ABC for 60 min at 56° C. The reduction solution was then replaced with 55 mM of iodoacetamide in 25 mM ABC and incubated for 45 min. The gel cubes were washed twice in 50 mM ABC and dehydrated with 100% ethanol. Thirty μL of modified sequencing-grade trypsin at a concentration of 5 μg/mL in 25 mM ABC buffer and 1 mM $CaCl_2$ was added and incubated at 4° C. for 30 min. Excess trypsin solution was removed and 15 μL of 25 mM ABC buffer was added. Digestion was carried out overnight at 37° C. and terminated by TFA addition to a final concentration of 0.1% v/v. The supernatant was then transferred to an eppendorf tube. To the gel pieces 50 μL of 50% ethanol in 0.1% TFA was added and sonicated for 15 min. The process was repeated and all supernatants derived from one gel section were pooled and dried to about 10 μL using a vacuum centrifuge.

1.4 Preparation of Samples for Quantitative ICAT Analysis

Protein labelling and separation were based on the geLC-MS/MS approach[33] using the cleavable ICAT reagent (Applied Biosystems). Protein was first precipitated using TCA (16%) and solubilised with 6 M urea, 5 mM EDTA, 0.05% SDS and 50 mM Tris-HCl pH 8.3. Protein concentration was determined using the BCA protein reagent and adjusted to 1 mg/ml. 100 μg of protein from each growth condition was individually reduced using 2 μL of 50 mM Tris(2-carboxyethyl)phosphine hydrochloride for 1 h at 37° C. Reduced protein from the haem-limitation growth condition was then alkylated with the $ICAT_{heavy}$ reagent and protein from haem-excess growth condition with the $ICAT_{light}$ reagent. The two samples were then combined and subjected to SDS-PAGE on a precast Novex 10% NUPAGE gel (Invitrogen). The gel was stained for 5 min using SimplyBlue™ SafeStain (Invitrogen) followed by destaining with water. The gel lane was then excised into 20 sections from the top of the gel to the dye front.

The excised sections were further diced into 1 $mm^3$ cubes and in-gel digested overnight and extracted twice according to the above procedure. The pooled supernatant was dried under reduced vacuum to about 50 μL followed by mixing with 500 μL of affinity load buffer before loading onto the affinity column as per manufacturer's instruction (Applied Biosystems). Eluted peptides were dried and the biotin tag cleaved with neat TFA at 37° C. for 2 h followed by drying under reduced vacuum. The dried samples were suspended in 35 μL of 5% acetonitrile in 0.1% TFA.

1.5 Liquid Chromatography and Mass Spectrometry

MS was carried out using an Esquire HCT ion trap mass spectrometer (Bruker Daltonics) coupled to an UltiMate Nano LC system (LC Packings—Dionex). Separation was achieved using a LC Packings reversed phase column (C18 PepMap100, 75 μm i.d.×15 cm, 3 μm, 100 Å), and eluted with 0.1% formic acid with the following acetonitrile gradient: 0-5 min (0%), 5-10 min (0-10%), 10-100 min (10-50%), 100-120 min (50-80%), 120-130 min (80-100%).

The LC output was directly interfaced to the nanospray ion source. MS acquisitions were performed under an ion charge control of 100000 in the m/z range of 300-1500 with maximum accumulation time of 100 ms. When using GPF three additional m/z ranges (300-800, 700-1200 and 1100-1500) were used to select for precursor ions and each m/z range was carried out in duplicate to increase the number of peptides identified. MS/MS acquisition was obtained over a mass range from 100-3000 m/z and was performed on up to 10 precursors for initial complete proteome analysis and 3 for ICAT analysis for the most intense multiply charged ions with an active exclusion time of 2 min.

1.6 Protein Identification for Non-Quantitative Proteome Analysis

Peak lists were generated using DataAnalysis 3.2 (Bruker Daltonics) using the Apex peak finder algorithm with a compound detection threshold of 10000 and signal to noise threshold of 5. A global charge limitation of +2 and +3 were set for exported data. Protein identification was achieved using the MASCOT search engine (MASCOT 2.1.02, Matrix Science) on MS/MS data queried against the *P. gingivalis* database obtained from The Institute for Genomic Research (TIGR) website (www.tigr.org). The matched peptides were further evaluated using the following criteria, i) peptides with a probability based Mowse score corresponding to a p-value of at most 0.05 were regarded as positively identified, where the score is $-\log\times 10(\log(P))$ and P is the probability that the observed match is a random event ii) where only one peptide was used in the identification of a specific protein and the MASCOT score was below 30, manual verification of the spectra was performed.

1.7 Protein Identification for ICAT

To increase confidence in the identification of ICAT-labeled proteins especially for those with single peptide hits, additional filters were applied as follows: i) the heavy and light peptides of an ICAT pair must have exhibited closely eluting peaks as determined from their extracted ion chromatograms ii) for proteins with a single unique peptide, this peptide must have been identified more than once (e.g in different SDS-PAGE fractions or in both the light and heavy ICAT forms iii) if a single peptide did not meet the criteria of (ii), the MASCOT score must have been ≥25, the expectation value ≤0.01 and the MS/MS spectrum must have exhibited a contiguous series of 'b' or 'y'-type ions with the intense ions being accounted.

1.8 Estimation of False Positive

To independently estimate the level of false positive assignments, a reverse database of *P. gingivalis* was created by reversing the order of the amino acid sequences for each protein such that the database is identical in size to the normal database in terms of the protein number, size and distribution of amino acids[34]. The false positive rate was thus estimated as $N_R/N_F$ where $N_R$=number of peptides identified with the reverse database (MASCOT score of peptide above threshold for the reverse database) and $N_F$=number of peptides identified with the normal database (MASCOT score of peptide above threshold for normal database). False positives were determined from the comprehensive proteome analysis ($N_F$=18375 peptides) and quantitative ICAT analysis ($N_F$=530 peptides).

1.9 Quantification of Relative Abundance

The ratio of isotopically heavy $^{13}C$ to light $^{12}C$ ICAT labelled peptides was determined using a script from DataAnalysis (Bruker Daltonics) and verified manually based on measurement of the monoisotopic peak intensity (signal intensity and peak area) in a single MS spectrum. The minimum ion count of parent ions used for quantification was 2000 although >96% of both heavy and light precursor ions were >10000. In the case of poorly resolved spectra, the ratio was determined from the area of the reconstructed extracted ion chromatograms (EIC) of the parent ions. Averages were calculated for multiple peptides derived from a single parent protein and outliers were removed using the Grubb's test with $\alpha$=0.05.

1.10 Genome Analysis

The cellular localisation of *P. gingivalis* proteins was predicted using CELLO (http://cello.life.nctu.edu.tw)[35] and transmembrane helices using TMHMM 2.0 (www.cbs.dtu.dk/services/TMHMM-2.0) based on the sequence obtained from TIGR. To estimate the relative expression level of the proteins identified as compared to the theoretical proteome CAI values were calculated based on the coding sequence of *P. gingivalis* from genebank (ftp://ftp.nchi.nih.gov/genbank/genomes/Bacteria/Porphyromonas_gingivalis_W83/) using the program INteractive Codon Analysis 1.12a (http://www.bioinfo-hr.orf/inca,[14] with ribosomal proteins and tRNA synthases being defined as highly expressed genes. Operon prediction was carried out from the Microbesonline website (http://microbesonline.org)[36].

1.11 Construction of ECR312 Mutant

*P. gingivalis* W50 Open Reading Frame PG1374 potentially encodes an immunoreactive 47 KDa antigen (PG97) based on the *P. gingivalis* W83 genome (www.tigr.org). To construct *P. gingivalis* PG1374 mutant, a 672 bp upstream fragment of the PG1374 gene with flanking ApaI and AatII restriction sites (underlined) was generated from the W50 genomic DNA by PCR with primers ECR312ApaI-For (5'-AGAGGGCCCTAGCAATCATTGCATTGCT-3') and ECR312AatII-Rev (5'-TGCGACGTCGTGTTACCAATAGAGGATT-3'). This fragment was cloned into AatII and BamHI sites on pAL30, pGem®T-easy (Promega) containing a subcloned ermF cassette[37] to create pAL36. Similarly, a 565 bp fragment downstream of PG1374 with flanking PstI and NdeI restrictions sites was amplified with ECR312PstI-For2 (5'-TGACTGCAGGCTTTCGACCTTGGATCTT-3') and ECR312NdeI-Rev2 (5'-TCGCATATGAAGAAATAAGTGCCGTCGG-3') primers, and cloned into PstI and NdeI restrictions sites in pAL36. The resulting plasmid having ermF cassette flanked with upstream and downstream fragments of the PG1374 open reading frame (designated as pAL36.1) was linearized with ScaI and transformed into *P. gingivalis* W50 as previously described[38]. Transformed cells were selected after 7 days of incubation at 37° C. under anaerobic conditions on HBA plate containing 10 μg mL$^{-1}$ erythromycin. Confirmation of DNA integration was performed by PCR analysis and the resulting mutant was designated as ECR312.

1.12 Antibiotic Protection Invasion Assay

To compare the invasion efficiencies of W50 and ECR312, an antibiotic protection assay was carried out as described previously in a 24-well cell culture plate[39]. Briefly, a fixed number of *P. gingivalis* cells were allowed to invade a KB monolayer (~$10^5$ cells in each well). Non invaded or adhered cells were killed by further incubation for 1 h with gentamicin (300 μg/mL) and metronidazole (200 μg/mL). Colony forming units of invaded bacteria were then enumerated on horse blood agar plates.

1.13 Cell Binding Assays

The cell binding assay was carried out as described previously[40]. Briefly, *P. gingivalis* was first grown to mid log phase to a cell density of ~$2.9\times 10^9$ cells/mL. The cells were then washed followed by labelling with 500 μg of fluorescein isothiocyanate (FITC) (Invitrogen) resuspended in 500 μL DMSO followed by incubation at 37° C. for 45 min with shaking. After incubation, the cells were further washed, resuspended in incomplete Earl's minimum essential medium (JRH Biosciences) and the *P. gingivalis* cells adjusted based on cell counts using a FACSCaliber flow cytometer (Becton Dickinson, San Jose, Calif.). The green emission of FITC was measured with a 525-nm filter (FL1). The multiparametric data were analyzed using CellQuest software (Becton Dickinson, San Jose, Calif.). All measurements were done in duplicate, and for quantitation of FITC fluorescence, mean fluorescence intensity (MFI) values were used.

Binding of the wild type *P. gingivalis* and ECR312 was carried out in parallel by inoculating 200 μL of cell suspension onto the KB cells at 5% $CO_2$ atmosphere at 37° C. for 40 min. Following incubation the supernatant containing the KB cells and bacteria were transferred to a 1.5 mL tube. The remaining bound cells were then detached off the well with 200 μL of Trypsin-EDTA mixture (JRH Bioscience) for 5 min at 37° C. and pooled with the corresponding collected supernatants. 500 μL of complete EMEM was then added to inactivate the trypsin followed by three washes and final suspension in 1 mL PBS. The bound cells were counted on the flow cytometer as described earlier.

2. Results and Discussion 2.1 Growth of *P. gingivalis* in Continuous Culture

When grown in continuous culture in a rich medium containing excess haem *P. gingivalis* W50 achieved a steady state cell density approximately 48 h after inoculation of 2.03±0.04 mg cellular dry weight/mL. When the concentration of haemin in the growth medium was decreased from 5.0 μg/ml to 0.1 μg/ml, a significantly lower steady state cell density of 0.99±0.20 mg cellular dry weight/mL was achieved demonstrating that haem availability was limiting growth. The effect of hacm-limitation on cell density was alleviated when haem was added back into the culture.

The growth of *P. gingivalis* during haem-limitation was in agreement with previous studies using chemostats with a *P. gingivalis* mean generation time of 6.9 h[41,42]. Due to the inability of *P. gingivalis* to synthesize PPIX, this essential nutrient is thought to be acquired through proteolysis of haemoglobin and other haem containing plasma proteins[9] and a deficiency in haem was thus reflected in the significantly lower cell density.

2.2 Proteome Analysis of *P. gingivalis* Grown Under Haem-Limitation

The proteome of *P. gingivalis* grown under haem-limitation was extensively analysed by two different approaches. Using in-solution digestion followed by LCMS with gas phase fractionation, 344 proteins were identified. In the geLCMS approach, 385 proteins were identified while 247 proteins were found by both approaches. With the combined strategy a total of 478 proteins were identified (see Table 1) with an estimated false positive rate of 0.4% calculated from searches against the *P. gingivalis* reverse database. 77.0% of all proteins were identified by ≥2 unique peptides or by ≥2 identical peptides from independent LCMS runs (from different m/z ranges or SDS PAGE bands). The 478 identified proteins represent ~25% of all the 1988 assigned protein-encoding genes identified by whole-genome analysis[43]. Although a quarter of the total predicted proteome was identified this figure is higher if the actual number of genes expressed during any one growth condition is taken into account. In *Pseudomonas aeruginosa* and *Bacillus subtilis* the percentage of total ORFs transcribed during a single growth condition was estimated to be 60% and 40%, respectively[44,45]. By examining the duty cycle limitation of their mass spectrometers Zhang and co-workers[46] estimated that around 60% of *P. gingivalis* predicted ORFs were expressed under their growth condition. Therefore based on these figures between 41-62% of *P. gingivalis* proteins expressed under the present growth conditions have been identified. The functional classification of the 478 identified proteins is shown in Table 1.

TABLE 1

Coverage of the theoretical proteome of *P. gingivalis* using the combined strategy shown in FIG. 1.

| Functional class of proteins[a] | Proteins ID/ Total Protein[b] | % of class ID |
|---|---|---|
| Energy metabolism | 78/140 | 55.7 |
| Protein synthesis | 68/117 | 58.1 |
| Fatty acid and phospholipid metabolism | 9/16 | 56.3 |
| Protein fate | 37/75 | 49.3 |
| Purines, pyrimidines, nucleosides, and nucleotides | 22/44 | 50.0 |
| Central intermediary metabolism | 11/23 | 47.8 |
| Cellular processes | 12/46 | 26.1 |
| Cell envelope | 32/140 | 22.8 |
| Amino acid biosynthesis | 2/19 | 10.5 |
| Signal transduction | 2/12 | 16.6 |
| Unknown function | 47/201 | 23.4 |
| Transcription | 7/31 | 22.6 |
| Transport and binding proteins | 20/119 | 16.8 |
| DNA metabolism | 14/81 | 17.3 |
| Biosynthesis of cofactors, prosthetic groups, and carriers | 14/88 | 15.9 |
| Hypothetical proteins (includes conserved) | 96/695 | 13.8 |
| Regulatory functions | 5/47 | 10.6 |
| Other categories | 2/134 | 1.5 |

[a]Functional classification data obtained from TIGR (www.tigr.org)
[b]Some proteins have been assigned to more than one functional class To date, there is only one reported attempt to identify *P. gingivalis* proteins globally using a multidimensional proteomics approach[46]. The present inventors have identified 478 *P. gingivalis* W50 proteins that were expressed during continuous culture under haem-limitation compared to the study of Zhang and co-workers[46] where 1014 *P. gingivalis* ATCC 33277 proteins were identified when this strain was cultured in keratinocyte growth medium and the same medium exposed to secreted epithelial cell components. As the strain used, the growth conditions and the processing of MS data were different in the two studies, it is difficult to make direct comparisons between the two datasets. Nevertheless, 75 proteins were uniquely identified in the present methods.

Using CELLO to predict the subcellular protein localisation, most of the proteins identified in this study were predicted to be from the cytoplasm (347 out of a predicted 1350 proteins), followed by the periplasmic space (48/113), outer membrane (47/154), inner membrane 1.5 (24/256) and extracellular (12/35). As expected, a low percentage of predicted inner membrane proteins were identified. To further increase the confidence of predicting inner membrane-proteins the Transmembrane Hidden Markov Model (TMHMM) was used. Using the TMHMM approach 20 out of the 242 proteins predicted to have >2 transmembrane domains (TMD) were identified and 5 out of 44 proteins predicted to have >10 TMDs were identified. Notably, all 12 of the membrane proteins with >10 transmembrane domains detected were identified from the in-solution digestion method.

2.3 Significance of Identified Proteins

Figure 2:
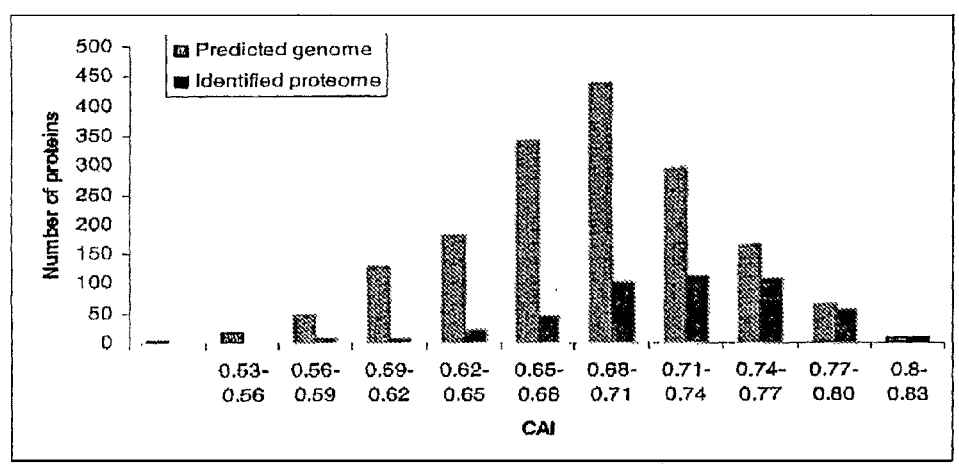
FIG. 2 shows a graph indicating the codon adaptation index (CAI) distribution of the identified *P. gingivalis* proteome and the predicted *P. gingivalis* genome calculated using INCA [14]. Ribosomal and tRNA synthases were defined as highly expressed genes. Genes with less than 100 codons were excluded, bringing the total calculated genes to 1685.

Highly expressed genes in many bacteria often have a strong composition bias in terms of codon usage. The Codon Adaptation Index (CAI) can be used to predict the expression level of a gene based on its codon sequence, with a higher CAI value indicating increased expression[47]. Of 1685 genes in the *P. gingivalis* genome that have >100 codons, almost 92% have CAI values between 0.62 and 0.80 (FIG. 2). Although this range is narrow compared with eukaryotic organisms (4) it is similar to the thermophile *Thermoanaerobacter tengcongensis* where 89% of the predicted genes have CAI values between 0.35 and 0.50[49]. The CAI values of the genes encoding the 478 identified proteins in this study have a similar distribution to the theoretical proteome although there was a bias towards the detection of higher abundance proteins. Despite this bias, a number of proteins encoded by genes of very low CAI were identified. This result clearly exemplifies the problem of the large dynamic range of protein abundance in cells, showing it is currently not possible to detect all proteins at once.

The functional classes of proteins with the highest percentage of identified proteins are those involved in energy metabolism (Table 1), typically those involved in fermentation (95%, CAI 0.70-0.80), glycolysis (82%, CAI 0.71-0.83) and metabolism of amino acids and amines (81%, CAI 0.71-0.84). This was largely expected as essential proteins involved in basic metabolic functions such as energy metabolism have been shown to be very abundant in the bacterial cell. Most importantly almost 90% of these proteins are predicted to be in the cytoplasm, which also made detection easier compared with membrane proteins. The functional classes of proteins represented least are those involved in transpositioning, hypothetical proteins and regulatory functions.

Although the complete genome of *P. gingivalis* has been sequenced, many critical questions regarding cellular functions remain unanswered. Proteomic studies that identify the translated gene products therefore help provide additional insights into the functional genome. For example *P. gingivalis* is known to be asaccharolytic[3] although the genome contains putative ORFs for all enzymes of the glycolytic pathway[43]. The poor utilization of this pathway has been attributed to the glucose kinase gene being interrupted by an insertion element[43]. In keeping with this finding glucose kinase, or another glycolysis-specific enzyme, phosphofructokinase was not identified. In contrast, all enzymes involved in gluconeogenesis were found, suggesting glucose necessary for processes such as polysaccharide biosynthesis may be derived via this pathway.

2.4 Response of *P. gingivalis* to Haem-Limitation as Determined Using ICAT

Figure 3:
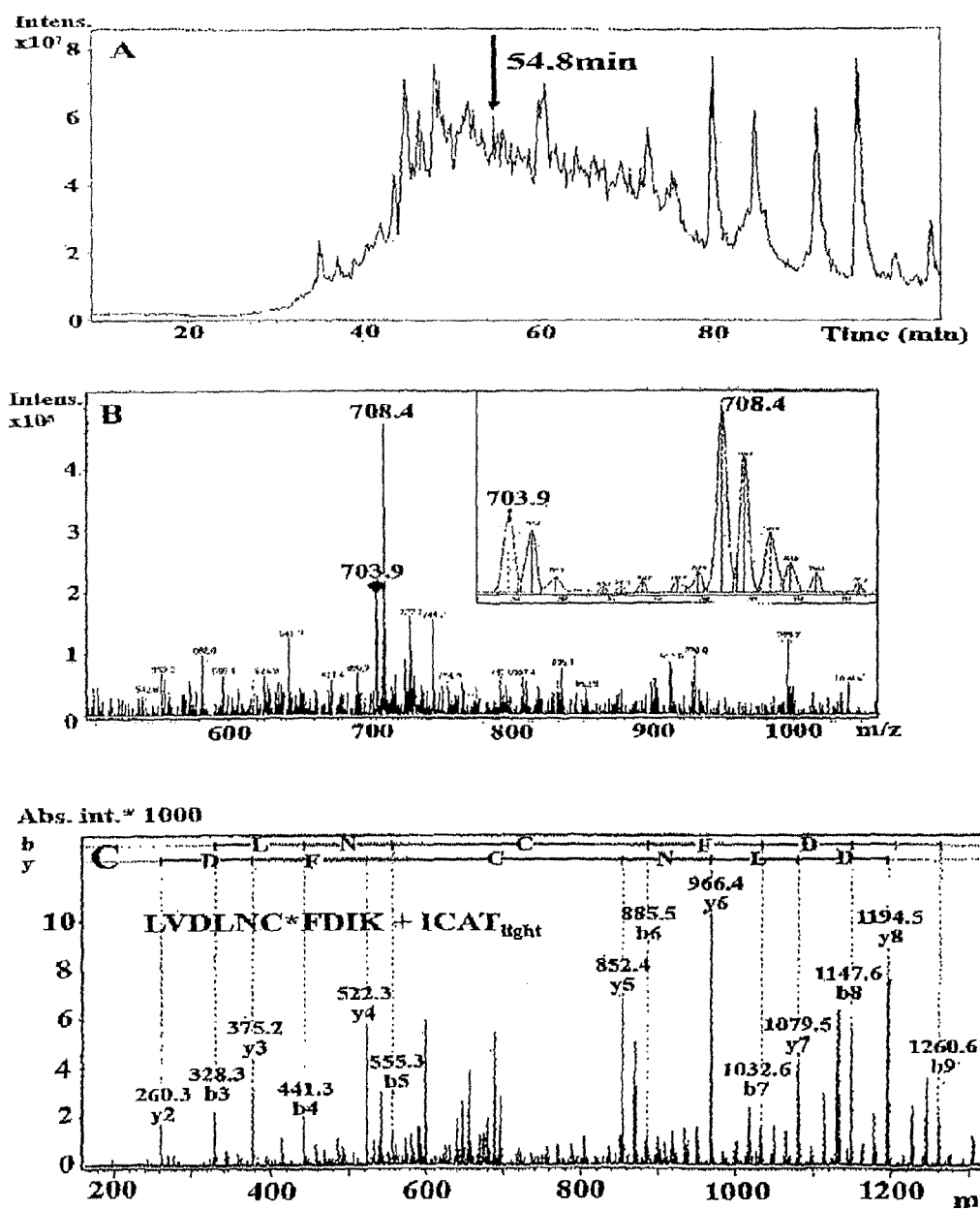
FIG. 3 shows the analysis and identification of PG0390 based on detection of a single peptide (A) Total ion chromatogram. (B) Mass spectrum at 54.8 min, insert showing an enlarged ICAT peptide ion pair at 703.9 and 708.4 m/z of ratio 1:2 (L/H). (C) Product ion spectrum for precursor 703.9 m/z. This peptide ion was identified as having the sequence LVDLNC*FDIK (MASCOT score=40; C* denotes ICAT modified cysteine).

To carry out the quantitative ICAT analysis of the *P. gingivalis* response to haem-limitation, the geLCMS approach was chosen, as the in-solution ICAT method was unsatisfactory due to the presence of strong interfering triply charged ions. The presence of these triply charged ions resulted in very low number of protein identifications. The ICAT labelled soluble and insoluble protein fractions were therefore independently separated by SDS-PAGE and each gel lane divided into 20 sections for in-gel tryptic digestion followed by affinity purification and LCMS. In total 142 proteins were identified. No matches to the reverse database were obtained indicating a low level of false positive identification. Considering proteins detected in both fractions, 53 proteins (34.0%) were identified based on the presence of two or more unique peptides with a probability based Mowse score corresponding to a p-value of at most 0.05, 60 proteins (38.5%) were identified based on the presence of one unique peptide identified from two or more different fractions or both ICAT labelling states (of those 58 have MASCOT score of ≥25) and 43 of the proteins (27.5%) were identified on the basis of a single unique peptide having a MASCOT score ≥25, expectation value of <0.01, a contiguous series of 'b' or 'y'-type ions and the intense ions being accounted for when interpreted manually. An example of a protein identification based on the analysis of a single unique peptide is shown in FIG. 3.

Figure 4:
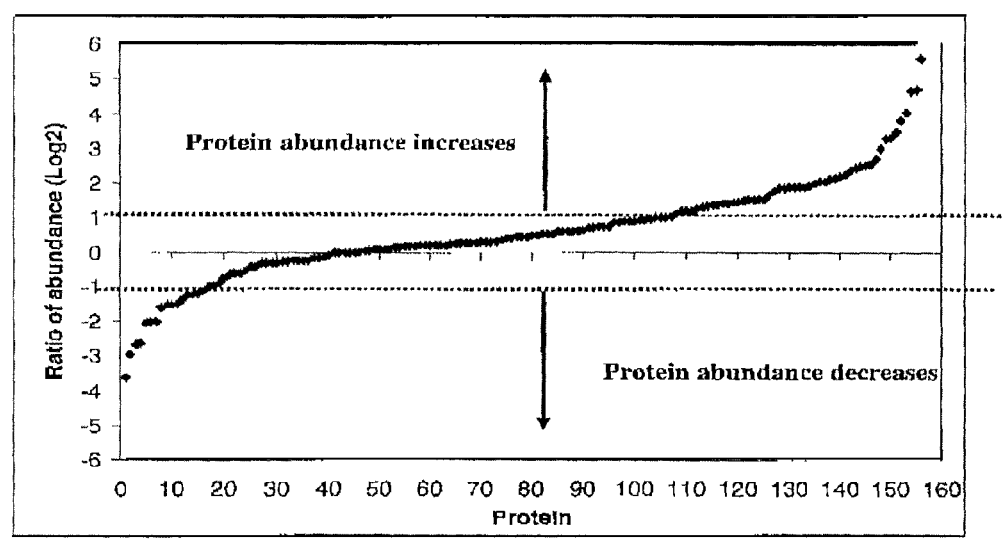
FIG. 4 shows the distribution of protein abundance based on ratio of haemn-limitation over hacm-excess (every one unit on the Log 2 scale indicates a two fold change).

Of the proteins identified, 103 were found in the soluble fraction, 53 in the insoluble fraction and 14 proteins in both fractions. In response to the change in environmental conditions from hacm-excess to haem-limitation 70 of the identified proteins exhibited at least a two-fold change in abundance (FIG. 4). Of these, the abundance of 53 proteins increased more than 2 fold and the abundance of 17 proteins decreased more than 2 fold during hacm-limitation. In order to assess the reproducibility of the present data and to increase protein identification for the insoluble fractions, cells were harvested from the chemostat on different days during haem-limitation and excess growth. A different extraction method followed by ICAT labelling was then repeated with modified protocols (not shown). The data obtained were reproducible with proteins showing similar abundance ratios for selected proteins shown in Table 2 (e.g. PG0695 L/H=1.1, relabelling=1.3; PG0350 L/H=3.2, relabelling=2.6; PG0159 L/H=2.0, relabelling=2.2; PG0232 L/H=0.4, relabelling=0.4). To further verify the data, the relative abundance of those identified proteins that are predicted to be encoded by genes forming an operon were compared[50]. Five groups of proteins were found to be encoded by predicted operons or by genes grouped at specific loci (Table 2-shaded). In each ease the abundance of the encoded proteins appeared to be similar. One of the predicted operons encodes the outer membrane proteins, Omp40 (P00694) and Omp41 (PG0695) whose abundance were unchanged at a ratio of 1.1 (haem-limitation/haem-excess, L/E). These proteins have high sequence similarity to the OmpA-like porins of Gram-negative 1.5 bacteria[51] and are thought to provide a physical linkage between the outer membrane and the peptidoglycan layer. These structural proteins would not be expected to vary in abundance with a change in environmental haem levels. The remaining four predicted operons were found to be associated with glutamate or aspartate catabolism.

TABLE 2

Expression data of selected proteins in *P. gingivalis* during growth in haem-limitation.

| Tigr No Acc# | Protein and peptide sequence identified | Score[1] | N[2] | n-ICAT[3] | Fold change[4] | SD (±) |
|---|---|---|---|---|---|---|
| | Proteinases | | | | | |
| 1 PG2024/ PG0506 | Arginine-specific protease (RgpA$_{Cat}$/RgpB) | 11 | 2 | | 0.39 | 0.1 |

TABLE 2-continued

Expression data of selected proteins in *P. gingivalis* during growth in haem-limitation.

| Tigr No | Acc# | Protein and peptide sequence identified | Score[1] | N[2] | n-ICAT[3] | Fold change[4] | SD (±) |
|---|---|---|---|---|---|---|---|
| | | .GQDEMNEILC*EK | 51/14 | | | | |
| | | .C*YDPGVTPK | 24/14 | | | | |
| 2 | PG2024/ PG0506 | Arginine-specific protease (RgpA/RgpB adhesins) | | 19 | 3 | 0.95 | 0.2 |
| | | .DAGMSAQSHEYC*VEVK | 34/15 | | | | |
| | | .EGLTATTFEEDGVAAGNHEYC*VEVK | 44/13 | | | | |
| | | .C*VNVTVNSTQFNPVK | 59/15 | | | | |
| 3 | PG0232 | Zinc carboxypeptidase | | 4 | 1 | 0.40 | 0.1 |
| | | .C*QILIENHDKR | 21/18 | | | | |
| | | .YPSLC*TTSVIGK | 56/19 | | | | |
| 4 | PG0026 | Hypothetical protein (Homology to Arg proteases) | | 5 | 2 | 0.46 | 0.1 |
| | | .C*VVNSPGGQTASMAK | 30/14 | | | | |
| | | .FSNLPVLGGESC*R | 58/14 | | | | |
| | | *Invasion related proteins* | | | | | |
| 5 | PG0350 | Internalin related protein | | 11 | 4 | 3.2 | 0.6 |
| | | .FVPYNDDEGGEEENVC*TTEHVEMAK | 35/13 | | | | |
| | | .IIMELSEADVEC*TIK | 46/14 | | | | |
| | | .ILHC*NNNQLTALNLSANTK | 23/15 | | | | |
| | | .LDLPANADIETLNC*SK | 52/13 | | | | |
| 6 | PG1374 | Immunoreactive 47KDa protein | | 5 | 2 | 6.5 | 0.7 |
| | | .GLSVLVC*IISNQIAGEEMTK | 27/15 | | | | |
| | | .NPNLTYLAC*PK | 61/13 | | | | |
| 7 | PG0159 | Endopeptidase PepO | | 6 | 1 | 2.0 | 0.3 |
| | | .METELAQIC*YSK | 55/13 | | | | |
| 8 | PG2132 | Fimbrillin FimA | | 2 | 1 | 0.50 | — |
| | | .YDASNELRPTILC*IYGK | 45/16 | | | | |
| | | *Iron transport and related proteins* | | | | | |
| 9 | PG1552 | HmuR | | 1 | 1 | 4.0 | — |
| | | .MNSDELFEEITYPGYTIC*R | 25/15 | | | | |
| 10 | PG1019 | Hypothetical protein | | 2 | 1 | 25.0 | — |
| | | .TYMIDTNDSENDC*IAR | 70/14 | | | | |
| 11 | PG1286 | Ferritin | | 2 | 1 | 1.2 | — |
| | | .FGSVLEVFQQVYEHEC*K | 73/13 | | | | |
| 12 | PG0090 | Dps family protein | | 3 | 1 | 1.1 | 0.1 |
| | | .EEHELVC*AASTLK | 36/13 | | | | |
| 13 | PG0618 | Alkyl hydroperoxide reductase subunit C | | 1 | 1 | 41.6 | — |
| | | .AAQYVAAHDGQVC*PAK | 36/15 | | | | |
| | | *Others* | | | | | |
| 14 | PG0694 | Omp40 | | 5 | 1 | 1.1 | 0.1 |
| | | .RPVSC*PECPEPTQPTVTR | 26/16 | | | | |

TABLE 2-continued

Expression data of selected proteins in P. gingivalis during growth in haem-limitation.

| Tigr No | Acc# | Protein and peptide sequence identified | Score[1] | N[2] | n-ICAT[3] | Fold change[4] | SD (±) |
|---|---|---|---|---|---|---|---|
| 15 | PG0695 | Omp41 .RPVSC*PECPEVTPVTK | 39/15 | 12 | 1 | 1.1 | 0.1 |

[1]Highest scoring peptide score/threshold score (P = 0.05)
[2]Total number of independent peptide identification events for each protein
[3]Number of unique ICAT labelled peptides identified for each protein
[4]Average ratios of all quantified peptides for each protein in fold change (Haem-limitation/excess)
*Denotes ICAT modified cysteine

2.5 Host Cell Invasion Related Proteins

Figure 5:
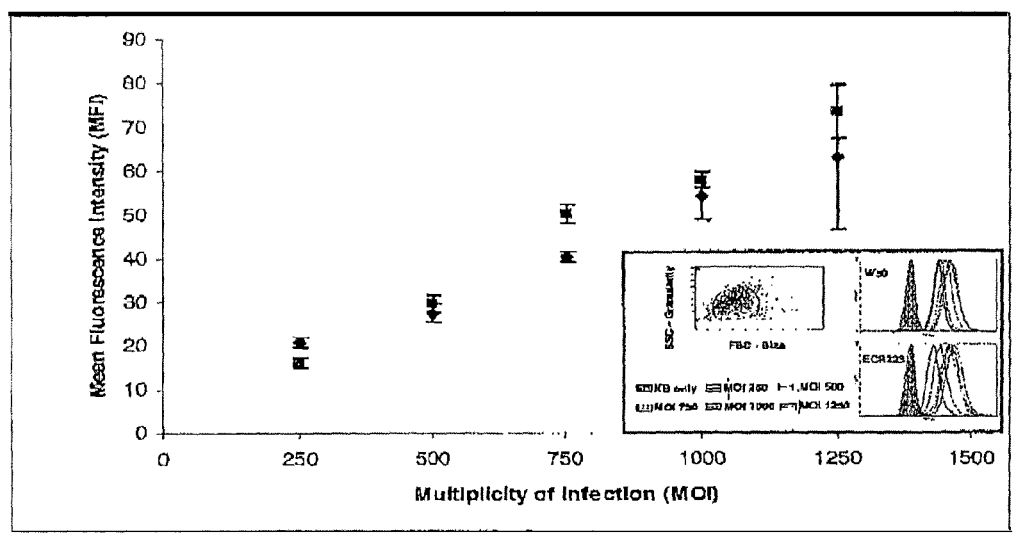
FIG. 5 shows binding to KB cells by *P. gingivalis* W50 (♦) and ECR312 (■). The assay was carried out with two biological replication (n=6). Insert shows the gating of live KB cells based on forward and side scattering properties (top left), five peaks representing FITC fluorescence of bound *P. gingivalis* W50 to KB cells at *P. gingivalis*:KB cell ratios of 250 to 1250 (top right) and ECR312 (bottom right).

Three proteins possibly involved in invasion of host cells, internalin related protein (PG0350), immunoreactive 47 kDa protein (PG1374) and endopeptidase PepO (PG0159) were higher in abundance during haem-limitation (Table 2). During an antibiotic protection invasion assay P. gingivalis lacking a functional PG1374 had approximately 50% lower invasion capability into epithelial cells as compared to the wild type (W50, 32625±2582 cfu/mL, ECR312 16250±1089 cfu/mL; p<0.01, Student's T-test). In a separate binding assay, there is no significance difference in the adherence of the PG1374 mutant as compared to the wild type W50 (FIG. 5).

PG1374 and PG0350 belong to a new class of cysteine containing protein with leucine rich repeat domains similar to the L. monocytogenes internalin protein InlJ[52]. In L. monocytogenes, there are at least fifteen members of the internalin family and all have been found to share certain structural features consisting of a signal peptide, N-terminal leucine rich repeat domain followed by a conserved inter-repeat region. Many of these proteins are involved in the cellular invasion process[53]. It has not been demonstrated why multiple internalins exist, but they are proposed to confer tropism toward different cell types[54].

The higher abundance of PG1374 and PG0350 during haem limitation (6.5 and 3.2 fold increase respectively) in the current work suggests the expression of these two proteins is stimulated during low hacm growth conditions. From the sequence information and predicted structure, more than half of the internalin LRR residues face outwards and are variable, suggesting them to be for protein-protein interaction surfaces specific to the different internalin classes[55]. PG1374 and PG0350 both possesses a signal peptide and are part of the novel class of up to 34 cell surface-located outer membrane proteins that have no significant sequence similarities apart from a conserved C-Terminal Domain (CTD) of approximately 80 residues[56]. In addition PG1374 is strongly immunogenic when probed with sera from human periodontitis patients[57] which further suggests it to be involved in cell surface protein interactions.

The process of internalization of P. gingivalis into gingival epithelial cells is thought to involve a coordinated process of attachment and invasion mediated by fimbriae and a variety of cell surface proteinases[58-60]. A P. gingivalis 33277 mutant lacking a functional putative internalin (PG0350) was shown to exhibit similar invasive characteristics but reduced biofilm formation capability compared to the wild type bacteria[46, 61]. The similar invasion was attributed to the presence of fimbriae that also play a role in epithelial cell invasion by strain 33277 although there is also a possibility that the similar invasiveness of this mutant was due to the presence of a second putative internalin protein (PG1374) encoded in the P. gingivalis genome. A double knockout of these two putative internalin proteins would potentially shed light on their possible cooperative invasive roles.

The 50% reduction in epithelial cell invasion by ECR 312 and no difference in cell binding clearly demonstrate that the observed reduced invasion into epithelial cells by P. gingivalis deficient in PG1374 is not due to lesser adherence but a real defect in the invasion process (FIG. 5). Bacterial invasion has been shown to be a highly complex process involving numerous proteins and receptors[62]. The involvement of multiple factors involved in P. gingivalis invasion has been demonstrated by Lamont's group at the University of Florida and includes haloacid dehalogenase, endopeptidases, a cation-transporting ATPase and an ATP-binding cassette transporter[60,63]. The discovery of PG1374 as an epithelial cell invasion related protein therefore adds to the list of proteins involved in this complex host cell invasion process by bacterial pathogens.

For many bacterial pathogens, it has been well established that iron availability influences virulence and the invasion process, but little is known about the influence of haem on the expression of P. gingivalis invasion genes. We were unable to perform binding and invasion assay on haem-limited cells because of the high mortality rate of the P. gingivalis from the oxidative stress likely due to lack of the protective layer of the p-oxo bis-haem form of iron PPIX[64-66]. However in this study, we have shown that the levels of the putative invasion related proteins PepO, PG0350 and PG1374 increased under haem-limitation and PG1374 is involved in the cell invasion.

These experiments described above are the first quantitative proteomic analysis of the response of P. gingivalis to a change in environmental conditions and demonstrates the utility of the stable isotope labelling approach combined with complete proteome analyses. P. gingivalis responds to limitation of the essential micronutrient hacm by increasing the abundance of a number of proteins linked to the oxidative stress response, virulence and invasion of host cells.

2.6 Cell Surface Located Protein PG1019

A P. gingivalis hypothetical protein, PG1019 was observed to be 25 times more abundant when the bacterium was grown under haem-limitation. Bioinformatic analyses suggest that PG1019 is a lipoprotein that is encoded by a gene located immediately upstream of a gene encoding a putative outer membrane receptor protein (PG1020) in a predicted operon. Multiple alignment (not shown) of PG1020 with known P. gingivalis TonB-linked outer membrane receptors shows the presence of a putative TonB box (residues 118-126), that is one of the characteristics of TonB-linked receptors[67] and a conserved region (residues 236-272) which Simpson and co-workers[68] refer to as the TonB box IV region. TonB-linked outer membrane receptors have been implicated with many iron, iron complex and other micronutrient uptake systems. The high abundance of PG1019 under haem limited growth conditions would be consistent with this protein being an accessory lipoprotein to a Ton-B linked system involved in the transport of iron/iron complexes into the cell or the sensing of environmental iron or iron complexes, although this remains to be demonstrated. In addition to the proteomic data a transcriptomic analysis using custom made *P. gingivalis* DNA microarrays of *P. gingivalis* W50 compared to a mutant lacking a function feoB1 gene (*P. gingivalis* FB1) was performed. The wild type W50 and FB1 mutant were both grown in continuous culture in haem excess conditions. *P. gingivalis* FB1 has approximately half the cellular iron content of the wild type W50[69]. Genes that show an increase in transcription are therefore likely to be upregulated in response to the decrease in intracellular or environmental iron content. Both PG1019 and PG1020 were significantly upregulated to similar levels in the FB1 mutant compared to the wild type. PG1019 showed a Log 2 increase of 2.46 and PG1020 showed a Log 2 increase of 2.33 at a significance level of P<0.05 in biological replicates, this is further evidence that these genes are located in an operon. Further a separate transcriptomic DNA microarray analysis of *P. gingivalis* W50 indicated that there was little or no expression of the PG1019 gene during haem-excess growth.

2.7 Alkyl Hydroperoxide Reductase Protein, AhpC (PG0618)

The most substantial change in *P. gingivalis* protein abundance during the transition from haem-excess to haem-limitation was observed with an alkyl hydroperoxide reductase protein, AhpC (PG0618, Table 2) which is a peroxide-scavenging enzyme that has been shown to play an important role in peroxide resistance in *P. gingivalis*[65]. In *P. gingivalis*, formation of a layer of the g-oxo bis-haem form of iron PPIX with oxygen on the cell surface is thought to act as an oxidative buffer due to its inherent catalase-like activity[11]. This layer may also serve as a cell surface storage of iron and PPIX[70]. During haem-limitation depletion of this source of iron PPIX was shown to result in an increased susceptibility to oxidative stress[64] The substantial increase in abundance of alkyl hydroperoxide reductase during haem-limitation could therefore be in response to the increased oxidative stress caused by the absence/reduction of the μ-oxo bishaem layer. OxyR an oxygen sensitive transcriptional activator also plays a role in the expression of alkyl hydroperoxide during anaerobic growth[71] where a *P. gingivalis* OxyR⁻ mutant shows decrease of 16 fold in gene expression. More recently Duran-Pinedo and co-workers also demonstrated the positive regulation of aphC expression by the RprY response regulator. The substantial increase in abundance thus suggests haem availability may have a role in RprY and OxyR-controlled gene expression. Interestingly the very high Codon Adaption Index (CAI) value of this protein (0.838) suggests this protein is able to be highly expressed in the cell for rapid induction in response to such stress.

Throughout this specification die word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed anywhere before the priority date of each claim of this application.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

REFERENCES

1. Albandar J M, Brunelle J A, Kingman A (1999). Destructive periodontal disease in adults 30 years of age and older in the United States et al., 1988-1994. *J. Periodontol.* 70:13-29.
2. Haffajee A D, Socransky S S (1994). Microbial etiological agents of destructive periodontal diseases, *Periodontol.* 2000 5:78-111.
3. Shah H, Gharbia S (1993). Batch culture and physiological properties. In: Biology of the species *Porphyromonas gingivalis*. Florida: Boca Raton CRC Press Inc, pp. 85-103.
4. Shizukuishi S, Tazaki K, Inoshita E, Kataoka K, Hanioka T, Amano A (1995). Effect of concentration of compounds containing iron on the growth of *Porphyromonas gingivalis*. *FEMS Microbial. Lett.* 131:313-7.
5. Schifferle R E, Shostad S A, Bayers-Thering M T, Dyer D W, Neiders M E (1996). Effect of protoporphyrin IX limitation on *Porphyromonas gingivalis*. *J. Endod.* 22.352-5.
6. Dashper S G, Cross K J, Slakecki N, Lissel P, Aulakh P, Moore C, et al. (2004). Hemoglobin hydrolysis and haem acquisition by *Porphyromonas gingivalis*. *Oral Microbiol. Immunol.* 19:50-6.
7. Shi Y, Ratnayake D B, Okamoto K, Abe N, Yamamoto K, Nakayama K (1999). Genetic analyses of proteolysis, hemoglobin binding, and hemagglutination of *Porphyromonas gingivalis*. Construction of mutants with a combination of rgpA, rgpB, kgp and hagA. *J. Biol. Chem.* 274:17955-60.
8. Genco C A, Simpson W, Forng R Y, Egal M, Odusanya B M (1995). Characterization of a Tn4351-generated hemin uptake mutant of *Porphyromonas gingivalis*: evidence for the coordinate regulation of virulence factors by hemin. *Infect. Immun.* 63:2459-66.
9. Bramanti T E, Holt S C (1991). Roles of porphyrins and host iron transport proteins in regulation of growth of *Porphyromonas gingivalis* W50. *J. Bacteriol.* 173:7330-9.
10. Brochu V, Grenier D, Nakayama K, Mayrand D (2001). Acquisition of iron from human transferrin by *Porphyromonas gingivalis*: a role for Arg- and Lys-gingipain activities. *Oral Microbiol. Immunol.* 16:79-87.
11. Smalley J W, Silver J, Marsh P J. Birss A J (1998). The periodontopathogen *Porphyromonas gingivalis* binds iron protoporphyrin IX in the mu-oxo dimeric form: an oxidative buffer and possible pathogenic mechanism. *Biochem. J.* 331 (Pt 3):681-5.
12. Moore W E, Moore L V (1994). The bacteria of periodontal diseases. *Periodontol.* 2000 5:66-77.
13. Dashper S G, Hendtlass A, Slakeski N, Jackson C, Cross K J, Brownfield L, et al. (2000). Characterization of a novel outer membrane hemin-binding protein of *Porphyromonas gingivalis*. *J. Bacteriol.* 182:6456-62.
14. Supek F, Vlahovicek K (2004). INCA: synonymous codon usage analysis and clustering by means of self-organizing map. *Bioinformatics* 20:2329-30.
15. Perbal J. (1984). A practical guide to molecular cloning, John Wiley and Sons (1984).

16. Sambrook J, Fritsch E F. Maniatis T. (1989). Molecular cloning: A laboratory manual, Cold Spring Habour Laboratory Press (1989).
17. Brown T A. (Editor) (1991). Essential Molecular Biology: A practical approach, Volumes 1 and 2, IRL Press (1991).
18. Glover M, Hames B D. (Editors) (1995 & 1996) DNA cloning: A practical approach, Volumes 1-4, IRL Press (1995 and 1996).
19, Ausubel, F M. (Editor) (1988). Current protocols in Molecular Biology, Greene. Associates and Wiley-Interscience (1988, including all updates until present).
20. Devereaux J, Haeberli P, Smithies O, (1984). A comprehensive set of sequence analysis programs for the VAX. *Nucleic Acids Res.* 12: 387-395.
21. Needleman S B and Wunsch C D, (1970). A general method applicable to the search for similarities in the amino acid sequence of two proteins. *J Mol. Biol.* 48(3): 443-53.
22. Thompson J D, Higgins D G, Gibson T J (1994). CLUSTAL W: improving the sensitivity of progressive multiple sequence alignment through sequence weighting, position-specific gap penalties and weight matrix choice. *Nucleic Acids Res.* 1994 Nov. 11; 22(22):4673-80
23. Cox & Coulter (1992). In: Wong W K (ed.) *Animals parasite control utilising technology.* Bocca Raton; CRC Press, 49-112.
24. Paoletti E & Panicali D. Modified vaccinia virus. U.S. Pat. No. 4,603,112.
25. Stocker B A D. Non-reventing live vaccines. U.S. Pat. No. 5,210,035.
26. Stocker B A D, Live vaccines comprising two mutations and foreign antigen. U.S. Pat. No. 4,837,151.
27. Stocker B A D. Novel non-reverting *Salmonella* live vaccines. U.S. Pat. No. 4,735,801.
28. Curtiss R. III, Goldschmidt R M., Norah B. Fletchall and Sandra M. Kelly (1988) Avirulent *Salmonella typhimurium* Δcya Δcrp oral vaccine strains expressing a streptococcal colonization and virulence antigen. *Vaccine* 6:155-160.
29. Jones P T, Dear, P H, Foote J, Neuberger M S, Winter G. (1986). Replacing the complementarity-determining regions in a human antibody with those from a mouse *Nature* 321:522-525.
30. Reichman L, Clark M, Waldman H, Winter G. (1988). Reshaping human antibodies for therapy. *Nature* 332: 323-327.
31. Carter P, Presta L, Gorman C M, Ridgway J B B, Henner D, et al. (1989). Humanization of an Anti-p185$^{HER}$2 Antibody for-Human Cancer Therapy. *Proc. Natl. Acad. Sci. USA* 89:4285-89.
32. Huse W D, Sastry L, Iverson S A, Kang A S, Alting-Mecs M, et al. (1989). Generation of a large combinatorial library of the immunoglobulin repertoire in phage lambda. *Science* 246:1275-1281.
33. Li J, Steen H, Gygi S P (2003). Protein profiling with cleavable isotope-coded affinity tag (clICAT) reagents: the yeast salinity stress response. *Mol. Cell. Proteomics* 2:1198-1204.
34. Peng J, Elias J E, Thoreen C C, Licklider L I, Gygi S P (2003). Evaluation of multidimensional chromatography coupled with tandem mass spectrometry (LC/LC-MS/MS) for large-scale protein analysis: the yeast proteome. *J. Proteome Res.* 2:43-50.
35. Yu C S, Lin C J, Hwang J K (2004). Predicting subcellular localization of proteins for Gram-negative bacteria by support vector machines based on n-peptide compositions. *Protein Sci.* 13:1402-6.
36. Alm E J, Huang K H, Price M N. Koche R P, Keller K, Dubchak I L et al. (2005). The MicrobesOnline Web site for comparative genomics. *Genome. Res.* 15:1015-22.
37. Fletcher H M, Schenkein H A, Morgan R M, Bailey K A, Berry C R and Macrina F L (1995). Virulence of a *Porphyromonas gingivalis* W83 mutant defective in the prtH gene. *Infect Immun.* 63:4:1521-1528.
38. Dashper S G, Brownfield L, Slakeski N, Zilm P S, Rogers A H, Reynolds E C (2001). Sodium ion-driven serine/threonine transport in *Porphyromonas gingivalis. J. Bacteriol.* 183:4142-8.
39, Lamont R J, Chan A, Belton C M, Izutsu K T, Vasel D, Weinberg A. (1995) *Porphyromonas gingivalis* invasion of gingival epithelial cells. *Infect Immun.* 63:1.0:3878-3885.
40. Pathirana R D, O'Brien-Simpson N M, Visvanathan K, Hamilton J A, Reynolds E C. (2007). Flow cytometric analysis of adherence of *Porphyromonas gingivalis* to oral epithelial cells. *Infect Immun.* 75:5:2484-2492.
41. Smalley J W, Birss A J, McKee A S, Marsh P D (1993). Haemin-binding proteins of *Porphyromonas gingivalis* W50 grown in a chemostat under haemin-limitation. *J. Gen. Microbiol.* 139:2145-50.
42. McKee A S, McDermid A S, Baskerville A, Dowsett A B, Ellwood D C, Marsh P D (1986). Effect of hemin on the physiology and virulence of *Bacteroides gingivalis* W50. *Infect. Immun.* 52:349-55.
43. Nelson K E, Fleischmann R D, DeBoy R T, Paulsen I T, Fouts D E, Eisen J A, et al. (2003). Complete genome sequence of the oral pathogenic Bacterium *Porphyromonas gingivalis* strain W83. *J. Bacteriol.* 185:5591-601.
44. Eymann C, Dreisbach A, Albrecht D, Bernhardt J, Becher D, Gentner S, et al. (2004). A comprehensive proteome map of growing *Bacillus subtilis* cells. *Proteomics* 4:2849-76.
45. Guina T, Purvine S O, Yi E C, Eng J, Goodlett D R, Aebersold R, et al. (2003). Quantitative proteomic analysis indicates increased synthesis of a quinolone by *Pseudomonas acruginosa* isolates from cystic fibrosis airways. *Proc. Natl. Acad. Sci. USA* 100:2771-6.
46. Zhang Y, Wang T, Chen W, Yilnaz O, Park Y, Jung I Y, et al. (2005). Differential protein expression by *Porphyromonas gingivalis* in response to secreted epithelial cell components. *Proteomics* 5:198-211.
47. Sharp P M, Li W H (1987). The codon Adaptation Index—a measure of directional synonymous codon usage bias, and its potential applications. *Nucleic. Acids Res.* 15:1281-95.
48. Washburn M P, Wolters D, Yates J R, 3rd (2001). Large-scale analysis of the yeast proteome by multidimensional protein identification technology. *Nat. Biotechnol.* 19:242-7.
49. Wang J, Xue Y, Feng X. Li X, Wang H, Li W, et al. (2004). An analysis of the proteomic profile for *Thermoanaerobacter tengcongensis* under optimal culture conditions. *Proteomics* 4:136-50.
50. Price M N, Huang K H, Aim E T, Arkin A P (2005). A novel method for accurate operon predictions in all sequenced prokaryotes. *Nucleic Acids Res.* 33:880-92.
51. Veith P D, Talbo G H, Slakeski N, Reynolds E C (2001). Identification of a novel heterodimeric outer membrane protein of *Porphyromonas gingivalis* by two-dimensional gel electrophoresis and peptide mass fingerprinting. *Eur. J. Biochem.* 268:4748-57.

52. Sabet C, Lecuit M, Cabanes D, Cossart P, Bierne H. (2005). LPXTG protein InlJ, a newly identified internalin involved in *Listeria monocytogenes* virulence. *Infect Immun.* 73:10:6912-6922.
53. Marino M, Braun L, Cossart P, Ghosh P (2000). A framework for interpreting the leucine-rich repeats of the *Listeria internalins*. *Proc Natl Acad Sci USA* 97:8784-8788.
54. Dramsi S, Biswas I, Maguin E, Braun L, Mastroeni P, Cossart P (1995). Entry of *Listeria monocytogenes* into hepatocytes requires expression of inlB, a surface protein of the internalin multigene family. *Mol. Microbiol.* 16:251-61.
55. Schubert W D, Urbanke C, Zichm T, Beier V, Machner M P, Domann E, Wehland J, Chakraborty T, Heinz D W. Structure of internalin, a major invasion protein of *Listeria monocytogenes*, in complex with its human receptor E-cadherin. *Cell.* 2002 Dec. 13; 111(6):825-836.
56. Seers C A, Slakeski N, Veith P D, Nikolof T, Chen Y Y, Dashper S G, Reynolds E C. (2006). The RgpB C-terminal domain has a role in attachment of RgpB to the outer membrane and belongs to a novel C-terminal-domain family found in *Porphyromonas gingivalis*. *J Bacterial.* 188 (17):6376-86.
57. Ross B C, Czajkowski L, Hocking D, Margetts M, Webb E, Rothel L, et al. (2001). Identification of vaccine candidate antigens from a genomic analysis of *Porphyromonas gingivalis*. *Vaccine.* 19(30):4135-4142.
58. Lamont R J, Oda D, Persson R E, Persson G R (1992). Interaction of *Porphyromonas gingivalis* with gingival epithelial cells maintained in culture. *Oral Microbiol Immunol* 7:364-367.
59. Chen T, Nakayama K, Belliveau L, Duncan M J (2001). *Porphyromonas gingivalis* gingipains and adhesion to epithelial cells. *Infect. Immun.* 69:3048-56.
60. Park Y, Yilmaz O, Jung I Y, Lamont R J (2004). Identification of *Porphyromonas gingivalis* genes specifically expressed in human gingival epithelial cells by using differential display reverse transcription-PCR. *Infect. Immun.* 72:3752-8.
61. Capestany C A, Kuboniwa M, Jung I-Y, Park Y, Tribble G D, Lamont R J. (2006). Role of the *Porphyromonas gingivalis* InlJ Protein in Homotypic and Heterotypic Biofilm Development. *Infect. Immun.* 74:5:3002-3005.
62. Cossart P, Sansonetti P J. (2004). Bacterial invasion: the paradigms of enteroinvasive pathogens. Science. 304:242-248.
63. Tribble G D, Mao S, James C E. Richard J. Lamont R J. (2006). A *Porphyromonas gingivalis* haloacid dehalogenase family phosphatase interacts with human phosphoproteins and is important for invasion *Proc Natl Acad Sci USA* 103:11027-11032.
64. Diaz P I, Rogers A H (2004). The effect of oxygen on the growth and physiology of *Porphyromonas gingivalis*. *Oral Microbiol. Immunol.* 19:88-94.
65. Okano S, Shibata Y, Shiroza T, Abiko Y. (2006). Proteomics-based analysis of a counter-oxidative stress system in *Porphyromonas gingivalis*. Proteomics. 6(1):251-258.
66. Smalley J W, Birss A J, Silver J, (2000). The periodontal pathogen *Porphyromonas gingivalis* harnesses the chemistry of the mu-oxo bishaem of iron protoporphyrin IX to protect against hydrogen peroxide. *FEMS Microbiol Lett.* 183(1):159-64.
67. Schramm E, Mende J, Braun V, Kamp R M (1987). Nucleotide sequence of the colicin B activity gene cba: consensus pentapeptide among TonB-dependent colicins and receptors. *J. Bacteriol.* 169:3350-3357.
68. Simpson W, Olczak T, Genco C A (2000). Characterization and expression of HmuR, a TonB-dependent hemoglobin receptor of *Porphyromonas gingivalis*. *J. Bacteriol.* 182:5737-5748.
69. Dashper S G, Butler C A, Lissel J P, Paolini R A, Hoffmann B, Veith P D, et al. (2005). A novel *Porphyromonas gingivalis* FeoB plays a role in manganese accumulation. *J. Biol. Chem.* 280(30):28095-28102.
70. Shah H N, Bonnett R, Mateen B, Williams R A (1979). The porphyrin pigmentation of subspecies of *Bacteroides melaminogenicus*. *Biochem. J.* 180:45-50.
71. Diaz P I, Slakeski N, Reynolds E C, Morona R, Rogers A H, Kolenbrander P E (2006). Role of oxyR in the oral anaerobe *Porphyromonas gingivalis*. *J Bacterial* 188: 2454-2462.
72. Duran-Pinedo A E, Nishikawa K, Duncan M J (2007). The RprY response regulator of *Porphyromonas gingivalis*. *Mol. Microbiol.* 64(5):1416

The invention claimed is:

1. A method of treating a subject having a *P. gingivalis* infection and/or periodontal disease comprising administering to the subject a composition comprising (a) an effective amount of a polypeptide that comprises the amino acid sequence of SEQ ID NO: 3 or a variant of SEQ ID NO: 3 consisting of conservative amino acid substitutions to SEQ ID NO: 3 that is at least 90% identical to SEQ ID NO: 3, wherein the variant polypeptide induces the production of an antibody that specifically binds to the polypeptide of SEQ ID NO:3 and (b) a pharmaceutically acceptable carrier.

2. The method according to claim 1, wherein the composition comprises said variant polypeptide at least 90% identical to SEQ ID NO: 3.

3. The method according to claim 1, wherein the composition comprises a variant polypeptide that is at least 95% identical to SEQ ID NO: 3.

4. The method according to claim 1, wherein the composition comprises a variant polypeptide that is at least 96% identical to SEQ ID NO: 3.

5. The method according to claim 1, wherein the composition comprises a variant polypeptide that is at least 97% identical to SEQ ID NO: 3.

6. The method according to claim 1, wherein the composition comprises a variant polypeptide that is at least 98% identical to SEQ ID NO: 3.

7. The method according to claim 1, wherein the composition comprises a variant polypeptide that is at least 99% identical to SEQ ID NO: 3.

8. The method according to claim 1, wherein the composition comprises a polypeptide comprising the amino acid sequence of SEQ ID NO:3.

* * * * *

SEQUENCE LISTING

```
<160> NUMBER OF SEQ ID NOS: 37

<210> SEQ ID NO 1
<211> LENGTH: 484
<212> TYPE: PRT
<213> ORGANISM: Porphyromonas gingivalis (PG0350)

<400> SEQUENCE: 1

Met Lys Arg Lys Pro Leu Phe Ser Ala Leu Val Ile Leu Ser Gly Phe
1               5                   10                  15

Phe Gly Ser Val His Pro Ala Ser Ala Gln Lys Val Pro Ala Pro Val
            20                  25                  30

Asp Gly Glu Arg Ile Ile Met Glu Leu Ser Glu Ala Asp Val Glu Cys
        35                  40                  45

Thr Ile Lys Ile Glu Ala Glu Asp Gly Tyr Ala Asn Asp Ile Trp Ala
    50                  55                  60

Asp Leu Asn Gly Asn Gly Lys Tyr Asp Ser Gly Glu Arg Leu Asp Ser
65                  70                  75                  80

Gly Glu Phe Arg Asp Val Glu Phe Arg Gln Thr Lys Ala Ile Val Tyr
```

85                  90                  95
Gly Lys Met Ala Lys Phe Leu Phe Arg Gly Ser Ser Ala Gly Asp Tyr
                100                 105                 110
Gly Ala Thr Phe Ile Asp Ile Ser Asn Cys Thr Gly Leu Thr Ala Phe
            115                 120                 125
Asp Cys Phe Ala Asn Leu Leu Thr Glu Leu Asp Leu Ser Lys Ala Asn
        130                 135                 140
Gly Leu Thr Phe Val Asn Cys Gly Lys Asn Gln Leu Thr Lys Leu Asp
145                 150                 155                 160
Leu Pro Ala Asn Ala Asp Ile Glu Thr Leu Asn Cys Ser Lys Asn Lys
                165                 170                 175
Ile Thr Ser Leu Asn Leu Ser Thr Tyr Thr Lys Leu Lys Glu Leu Tyr
                180                 185                 190
Val Gly Asp Asn Gly Leu Thr Ala Leu Asp Leu Ser Ala Asn Thr Leu
            195                 200                 205
Leu Glu Glu Leu Val Tyr Ser Asn Asn Glu Val Thr Thr Ile Asn Leu
        210                 215                 220
Ser Ala Asn Thr Asn Leu Lys Ser Leu Tyr Cys Ile Asn Asn Lys Met
225                 230                 235                 240
Thr Gly Leu Asp Val Ala Ala Asn Lys Glu Leu Lys Ile Leu His Cys
                245                 250                 255
Asn Asn Asn Gln Leu Thr Ala Leu Asn Leu Ser Ala Asn Thr Lys Leu
            260                 265                 270
Thr Thr Leu Ser Phe Phe Asn Asn Glu Leu Thr Asn Ile Asp Leu Ser
        275                 280                 285
Asp Asn Thr Ala Leu Glu Trp Leu Phe Cys Asn Gly Asn Lys Leu Thr
    290                 295                 300
Lys Leu Asp Val Ser Ala Asn Ala Asn Leu Ile Ala Leu Gln Cys Ser
305                 310                 315                 320
Asn Asn Gln Leu Thr Ala Leu Asp Leu Ser Lys Thr Pro Lys Leu Thr
                325                 330                 335
Thr Leu Asn Cys Tyr Ser Asn Arg Ile Lys Asp Thr Ala Met Arg Ala
            340                 345                 350
Leu Ile Glu Ser Leu Pro Thr Ile Thr Glu Gly Gly Arg Phe Val
        355                 360                 365
Pro Tyr Asn Asp Asp Glu Gly Gly Glu Glu Asn Val Cys Thr Thr
    370                 375                 380
Glu His Val Glu Met Ala Lys Ala Lys Asn Trp Lys Val Leu Thr Ser
385                 390                 395                 400
Trp Gly Glu Pro Phe Pro Gly Ile Thr Ala Leu Ile Ser Ile Glu Gly
                405                 410                 415
Glu Ser Glu Tyr Ser Val Tyr Ala Gln Asp Gly Ile Leu Tyr Leu Ser
            420                 425                 430
Gly Met Glu Gln Gly Leu Pro Val Gln Val Tyr Thr Val Gly Gly Ser
        435                 440                 445
Met Met Tyr Ser Ser Val Ala Ser Gly Ser Ala Met Glu Ile Gln Leu
    450                 455                 460
Pro Arg Gly Ala Ala Tyr Val Val Arg Ile Gly Ser His Ala Ile Lys
465                 470                 475                 480

Thr Ala Met Pro

<210> SEQ ID NO 2
<211> LENGTH: 428

-continued

<212> TYPE: PRT
<213> ORGANISM: Porphyromonas gingivalis (PG1374)

<400> SEQUENCE: 2

```
Met Lys Leu Ser Ser Lys Lys Ile Leu Ala Ile Ile Ala Leu Leu Thr
1               5                   10                  15

Met Gly His Ala Val Gln Ala Gln Phe Val Pro Ala Pro Thr Thr Gly
            20                  25                  30

Ile Arg Met Ser Val Thr Thr Thr Lys Ala Val Gly Glu Lys Ile Glu
        35                  40                  45

Leu Leu Val His Ser Ile Glu Lys Lys Gly Ile Trp Ile Asp Leu Asn
    50                  55                  60

Gly Asp Ala Thr Tyr Gln Gln Gly Glu Glu Ile Thr Val Phe Asp Glu
65                  70                  75                  80

Ala Tyr His Glu Tyr Thr Ile Gly Thr Gln Thr Leu Thr Ile Tyr Gly
                85                  90                  95

Asn Thr Thr Arg Leu Gly Cys Arg Ser Thr Gly Ala Thr Ala Val Asp
            100                 105                 110

Val Thr Lys Asn Pro Asn Leu Thr Tyr Leu Ala Cys Pro Lys Asn Asn
        115                 120                 125

Leu Lys Ser Leu Asp Leu Thr Gln Asn Pro Lys Leu Leu Arg Val Trp
    130                 135                 140

Cys Asp Ser Asn Glu Ile Glu Ser Leu Asp Leu Ser Gly Asn Pro Ala
145                 150                 155                 160

Leu Ile Ile Leu Gly Cys Asp Arg Asn Lys Leu Thr Glu Leu Lys Thr
                165                 170                 175

Asp Asn Asn Pro Lys Leu Ala Ser Leu Trp Cys Ser Asp Asn Asn Leu
            180                 185                 190

Thr Glu Leu Glu Leu Ser Ala Asn Pro Arg Leu Asn Asp Leu Trp Cys
        195                 200                 205

Phe Gly Asn Arg Ile Thr Lys Leu Asp Leu Ser Ala Asn Pro Leu Leu
    210                 215                 220

Val Thr Leu Trp Cys Ser Asp Asn Glu Leu Ser Thr Leu Asp Leu Ser
225                 230                 235                 240

Lys Asn Ser Asp Val Ala Tyr Leu Trp Cys Ser Ser Asn Lys Leu Thr
                245                 250                 255

Ser Leu Asn Leu Ser Gly Val Lys Gly Leu Ser Val Leu Val Cys His
            260                 265                 270

Ser Asn Gln Ile Ala Gly Glu Glu Met Thr Lys Val Val Asn Ala Leu
        275                 280                 285

Pro Thr Leu Ser Pro Gly Ala Gly Ala Gln Ser Lys Phe Val Val Val
    290                 295                 300

Asp Leu Lys Asp Thr Asp Glu Lys Asn Ile Cys Thr Val Lys Asp Val
305                 310                 315                 320

Glu Lys Ala Lys Ser Lys Asn Trp Arg Val Phe Asp Phe Asn Gly Asp
                325                 330                 335

Ser Asp Asn Met Leu Pro Tyr Glu Gly Ser Pro Thr Ser Asn Leu Ala
            340                 345                 350

Val Asp Ala Pro Thr Val Arg Ile Tyr Pro Asn Pro Val Gly Arg Tyr
        355                 360                 365

Ala Leu Val Glu Ile Pro Glu Ser Leu Leu Gly Gln Glu Ala Ala Leu
    370                 375                 380

Tyr Asp Met Asn Gly Val Lys Val Tyr Ser Phe Ala Val Glu Ser Leu
385                 390                 395                 400
```

```
Arg Gln Asn Ile Asp Leu Thr His Leu Pro Asp Gly Thr Tyr Phe Phe
                405                 410                 415

Arg Leu Asp Asn Tyr Thr Thr Lys Leu Ile Lys Gln
            420                 425

<210> SEQ ID NO 3
<211> LENGTH: 393
<212> TYPE: PRT
<213> ORGANISM: Porphyromonas gingivalis (PG1019)

<400> SEQUENCE: 3

Met Lys Lys Asn Phe Leu Phe Phe Ser Leu Val Leu Ala Ala Ile Met
1               5                   10                  15

Ser Leu Leu Ser Ser Cys Ala Lys Asp Thr Pro Asp Ala Pro Glu Gln
            20                  25                  30

Tyr Ala Ile Thr Ile Arg Ala Lys Leu Pro Glu Gly Ser Thr Ile Glu
        35                  40                  45

Ser Leu Ala Gly Ile Ala Ile Glu Phe Leu Asp Leu Arg Thr Gln Gln
    50                  55                  60

Lys Val Glu Lys Gln Leu Asp Lys Ala Gly Val Cys Ser Leu Ser Leu
65                  70                  75                  80

Asp Ala Ser Val Tyr Thr Ile Thr Ile Arg Gly Glu Ile Gly Asn Asn
                85                  90                  95

Ser Ile Val Ala Ile Lys Glu Asn Tyr Ser Ile Ala Glu Asn Thr Thr
            100                 105                 110

Leu Glu Leu Pro Leu Ile Val Thr Lys Ile Arg Pro Ser Gly Leu Leu
        115                 120                 125

Phe Lys Glu Val Phe Phe Asn Gly Glu Thr Asn Asn Gly Gln Met Met
    130                 135                 140

His Pro Asp Gln Tyr Phe Val Ile Tyr Asn Asn Ser Asp Lys Val Val
145                 150                 155                 160

Tyr Ala Asp Gly Val Ala Phe Gly Leu Ala Ala His Ala Asn Val Thr
                165                 170                 175

Gly Glu Asp Ala Phe Thr Glu Glu Leu Thr Lys Asn Asn Arg Ile Val
            180                 185                 190

Leu Ser Met Ile Tyr Thr Ile Pro Gly Asn Gly Ser Gln Tyr Pro Ile
        195                 200                 205

Gln Pro Gly Gly Gln Leu Val Ile Ala Gly Thr Ala Ile Asn His His
    210                 215                 220

Asp Ala Glu His Pro Asn Ser Val Asp Leu Ser Gly Ala Asp Leu Glu
225                 230                 235                 240

Val Tyr Glu Pro Asp Gln Pro Ala Asn Phe Gly Gln Asp Val Asp Asn
                245                 250                 255

Pro Asn Val Pro Asn Met Val Lys Ile Phe Asn Arg Phe Gly Val Phe
            260                 265                 270

Met Met His Pro Arg Gly Phe Ile Pro Pro Val Leu Phe Glu Ile Asp
        275                 280                 285

Glu Pro Ile Glu Thr Phe Leu Ala Lys Asn Gln Phe Glu Tyr Thr Asn
    290                 295                 300

Asn Asp Gly Glu Asn Ile Met Leu Tyr Ala Val Pro Val Glu Asn Val
305                 310                 315                 320

Leu Asp Gly Ile Glu Thr Ala Asn Thr Gly Asn Met Lys Val Lys Ser
                325                 330                 335

Leu Pro Val Thr Val Asp Lys Ser Met Ile Gly Val Pro Gly Cys His
```

```
                    340             345             350
Arg Gly Ile Leu Ile Leu Arg Lys Thr Glu Glu Lys Asn Gly Arg Thr
            355                 360                 365

Tyr Met Ile Asp Thr Asn Asp Ser Glu Asn Asp Cys Ile Ala Arg Gln
        370                 375                 380

Gly Gln Asn Ser Phe Pro Ala Arg Phe
385                 390

<210> SEQ ID NO 4
<211> LENGTH: 188
<212> TYPE: PRT
<213> ORGANISM: Porphyromonas gingivalis (PG0618)

<400> SEQUENCE: 4

Met Thr Pro Ile Leu Asn Thr Val Phe Pro Glu Phe Lys Leu Asn Ala
1               5                   10                  15

Tyr His Asn Gly Glu Phe Lys Val Ile Thr Asn Glu Asp Leu Lys Gly
            20                  25                  30

Lys Trp Ser Leu Val Val Phe Tyr Pro Gly Asp Phe Thr Phe Val Cys
        35                  40                  45

Pro Thr Glu Leu Glu Asp Leu Ala Asn Lys Tyr Glu Glu Phe Lys Gln
    50                  55                  60

Leu Gly Val Glu Val Tyr Ser Cys Ser Cys Asp Thr His Phe Val His
65                  70                  75                  80

Lys Ala Trp Ala Asp Ala Ser Pro Ala Ile Lys Lys Val Gln Tyr Pro
                85                  90                  95

Met Leu Ala Asp Pro Ser Gly Ala Leu Thr Arg Asp Leu Gly Ile Leu
            100                 105                 110

Ile Asp Asp Val His Met Ala Tyr Arg Gly Ser Phe Val Ile Asn Pro
        115                 120                 125

Glu Gly Ile Ile Lys Ile Val Glu Leu Asn Asp Asn Ser Val Gly Arg
    130                 135                 140

Asp Ala Glu Glu Ile Leu Arg Lys Ile Lys Ala Ala Gln Tyr Val Ala
145                 150                 155                 160

Ala His Asp Gly Gln Val Cys Pro Ala Lys Trp Arg Glu Gly Gln Gln
                165                 170                 175

Thr Leu Lys Pro Ser Ile Asp Leu Val Gly Lys Ile
            180                 185

<210> SEQ ID NO 5
<211> LENGTH: 1455
<212> TYPE: DNA
<213> ORGANISM: Porphyromonas gingivalis (PG0350)

<400> SEQUENCE: 5
atgaaaagaa aaccgctatt ctcagcccctt gtaatccttt ccggcttctt cggatcggtt      60
cacccggcct cagcacagaa agttcctgca cccgtcgatg gcgagcgcat tatcatggag     120
ctaagtgaag ccgatgtgga gtgtacaatc aaaatagaag ccgaggatgg ctatgccaac     180
gacatttggg cagacctcaa cggaaacggc aagtacgatt cggggggagag gctcgattca     240 ggtgagtttc gtgatgttga gttcagacaa acaaaggcca tcgtctatgg caaaatggcc     300
aaattcttgt ttagaggttc ttctgcaggg gactatggtg ctaccttttat agatattagc     360 aattgtaccg gcctgactgc tttcgactgc tttgccaatc tgctgacaga actcgatctg     420
tccaaagcaa acggtctgac ttttgtaaac tgcggcaaaa accagctgac caagcttgac     480
```

```
ctgcccgcaa atgcggacat tgagacgctg aactgctcca aaaacaagat aacgagtctc    540
aacctatcga cctataccaa gctgaaagag ctttatgtgg cgacaacgg gctgacagcc      600 ttggatctct ccgccaatac gctcctcgaa gagctggtgt attctaacaa cgaggtgact    660
acgataaacc tgtctgccaa tacgaacttg aaaagcctgt attgcataaa caataagatg    720
accggactcg atgtcgcagc caacaaagag ctgaaaatac tccactgcaa caacaatcag    780
ctgaccgccc tcaatctctc ggccaatacc aagctgacga ctctaagctt cttcaacaac    840
gagctgacaa atatcgatct ctccgacaac acggctttgg agtggctttt ctgcaacggc    900
aataagctga cgaagttaga tgtatctgcc aacgccaatc tgatagcact gcaatgcagc    960
aacaaccagc tgactgctct ggatctgtca aaaacgccga aactgacaac gttgaattgc   1020
tactccaacc ggatcaaaga taccgccatg cgtgcattga tcgaaagcct gcctacgatc   1080
actgaaggag aaggcaggtt cgttccttac aacgacgatg aaggaggaga agaggagaac   1140
gtgtgtacaa ccgaacacgt ggaaatggcc aaggccaaga attggaaggt acttacctcg   1200
tggggagagc ctttccccgg aataacggct ttgatttcca tcgaaggtga gagcgaatat   1260
tccgtatatg ctcaagatgg catcctctac ctctccggta tggagcaggg cttgcccgtt   1320
caggtatata ccgtggggagg aagcatgatg tactcatctg tcgcttccgg atcagccatg   1380
gaaatacagc tcccgagagg tgcagcctat gtagtacgta tcggcagcca tgcgatcaaa   1440
accgcgatgc cgtaa                                                    1455

<210> SEQ ID NO 6
<211> LENGTH: 1287
<212> TYPE: DNA
<213> ORGANISM: Porphyromonas gingivalis (PG1374)

<400> SEQUENCE: 6
atgaaacttt catctaagaa aatcttagca atcattgcat tgctgacgat gggacatgct     60
gtgcaggcac agtttgttcc ggctcccacc acagggattc gcatgtctgt cactacaacc    120
aaggccgtag gcgaaaaaat cgaattgttg gttcattcca tagagaagaa aggcatctgg    180
atcgatctca atggggatgc cacttaccaa caaggagagg aaataaccgt attcgatgag    240
gcataccacg aatacacgat cgggacgcaa accctcacta tctatggtaa tacgacccga    300
ttgggctgtc gatctaccgg tgcaacggct gtcgatgtaa cgaaaaaccc taatctgacc    360
tatctcgcat gcccgaaaaa taatctgaaa tcattggact tgacgcaaaa cccaaagctg    420
ctgcgagttt ggtgcgactc taacgaaata gaaagtttgg acctgagtgg caatccggct    480
ttgatcatcc tcggctgtga caggaataag ctgactgagc tgaagaccga taacaacccc    540
aagttggcct ctctttggtg ttctgataat aacctgacgg agttggaact cagtgccaat    600
cctcgtctca atgatctttg gtgcttcggt aatcggatca cgaaactcga tctgagtgcc    660
aatcctctat tggtaacact tggtgcagtc gacaatgagc tttcgacctt ggatctttcc    720
aagaattcgg acgttgctta cctttggtgc tcatcgaaca aacttacatc cttgaatctg    780 tcggggggtga agggactgag tgtttttggtt tgtcattcca atcagatcgc aggtgaagaa    840
atgacgaaag tggtgaatgc tttgcccaca ctatctcccg cgcaggcgc tcagagcaag    900 ttcgtcgttg tagacctcaa ggacactgat gagaagaata tctgtaccgt aaaggatgtg    960
gaaaaagcta aaagtaagaa ctggcgagta tttgacttca acggtgattc tgacaatatg   1020
cttccatacg aaggaagtcc gacatcgaac ttggcagtag atgctcccac tgtcaggata   1080
tatcccaatc cggtaggaag atatgcgctc gtcgagatcc ccgagtctct tttagggcag   1140
```

```
gaagctgctt tatacgatat gaatggggta aaagtctata gtttcgcggt agagtctctt    1200
cgtcagaaca ttgacctgac acatcttccc gacggcactt atttcttccg tctcgataac    1260
tataccacta agctcatcaa acagtag                                         1287
```

<210> SEQ ID NO 7
<211> LENGTH: 1182
<212> TYPE: DNA
<213> ORGANISM: Porphyromonas gingivalis (PG1019)

<400> SEQUENCE: 7

```
atgaaaaaaa attttctttt tttctccctc gttttagcag ccatcatgtc gttgctgtca      60
tcttgtgcca aggatacgcc ggatgcgccc gaacagtacg ctatcactat ccgtgccaaa     120
ctaccggaag cagtacgat agagagtctc gcaggtatag ccatcgaatt cctcgatctt     180
cgtacccaac agaaagtgga aaaacagctc gacaaagccg tgtttgctc tcttagtctg      240 gatgccagtg tatatacgat tacgatacgt ggcgaaatag ggaacaacag tatcgttgcc     300
atcaaggaaa actattccat cgcagagaat actaccttgg agcttccact cattgtgacg     360
aagatccgcc cttccggtct gctgttcaaa gaagtatttt tcaatggaga gaccaacaac    420
gggcagatga tgcacccgga tcagtacttc gtcatataca ataatagcga taggtggtc     480 tatgccgatg tgtcgcttt cggtcttgcc gcacatgcca acgtaacagg tgaagacgct     540
ttcaccgagg agttgaccaa gaacaaccgc atcgtccttt ccatgatcta taccattccc     600
ggcaacggtt cgcagtatcc catccaaccc ggtggtcagc tcgtgatagc cggaacggcc     660
atcaatcacc acgatgccga gcatccgaat tccgtggact tgagcggtgc cgatttggaa    720
gtctatgagc cggatcagcc cgcaaacttc ggacaggatg tggacaaccc caatgttccc     780
aatatggtga agatatttaa tcgattcggt gttttcatga tgcatcccag aggatttatc     840
cctcctgttc ttttcgagat agatgagccg atcgagactt tcctggccaa gaaccagttc     900
gagtacacga acaatgatgg agagaacatt atgctctatg ccgttccggt ggaaaatgtg     960
ttggatggta tcgagaccgc caataccggt aatatgaaag tcaagtccct gcccgtgaca    1020
gtggataagt ccatgatcgg tgtaccgggt tgccaccgtg gcatactcat tcttcgcaag    1080
acggaagaaa agaatggccg tacctatatg atcgacacca acgactctga aaatgactgt    1140
atagcccgtc aaggacaaaa ctcttttcct gcaagattct aa                        1182
```

<210> SEQ ID NO 8
<211> LENGTH: 567
<212> TYPE: DNA
<213> ORGANISM: Porphyromonas gingivalis (PG0618)

<400> SEQUENCE: 8

```
atgactccta tcctgaacac cgttttcccc gagttcaaac tcaatgccta tcacaatggc     60
gaattcaaag taatcaccaa cgaagacttg aaaggcaagt ggtctttggt cgttttctat    120
cccggtgact ttacctttgt atgcccgacg gaattggaag acctggccaa taaatatgaa    180
gaattcaagc aacttggagt agaggtttac tcttgcagtt gcgatacccca cttcgtacac    240 aaggcttggg ccgacgcttc tcctgctatc aagaaggtac agtatccat gttggccgat    300 ccctccggtg cactcactcg cgatctgggt atcctgatcg atgatgttca tatggcttac    360
cgtggctctt tcgtgattaa ccccgaaggc attatcaaaa tcgtagagct gaacgacaac    420
agcgtaggcc gtgatgcaga agagatcctc cgtaagatca aggctgcaca atacgtagct    480
```

```
gctcacgatg gtcaggtatg tccggccaag tggcgtgaag gtcagcagac actgaaaccg      540
agcattgatc tcgttggtaa gatctaa                                          567
```

<210> SEQ ID NO 9
<211> LENGTH: 10
<212> TYPE: PRT
<213> ORGANISM: Porphyromonas gingivalis

<400> SEQUENCE: 9

Leu Val Asp Leu Asn Cys Phe Asp Ile Lys
1               5                   10

<210> SEQ ID NO 10
<211> LENGTH: 28
<212> TYPE: DNA
<213> ORGANISM: Artificial Sequence
<220> FEATURE:
<223> OTHER INFORMATION: Primer

<400> SEQUENCE: 10

```
agagggccct agcaatcatt gcattgct                                          28
```

<210> SEQ ID NO 11
<211> LENGTH: 28
<212> TYPE: DNA
<213> ORGANISM: Artificial Sequence
<220> FEATURE:
<223> OTHER INFORMATION: Primer

<400> SEQUENCE: 11

```
tgcgacgtcg tgttaccaat agaggatt                                          28
```

<210> SEQ ID NO 12
<211> LENGTH: 28
<212> TYPE: DNA
<213> ORGANISM: Artificial Sequence
<220> FEATURE:
<223> OTHER INFORMATION: Primer

<400> SEQUENCE: 12

```
tgactgcagg ctttcgacct tggatctt                                          28
```

<210> SEQ ID NO 13
<211> LENGTH: 28
<212> TYPE: DNA
<213> ORGANISM: Artificial Sequence
<220> FEATURE:
<223> OTHER INFORMATION: Primer

<400> SEQUENCE: 13

```
tcgcatatga agaaataagt gccgtcgg                                          28
```

<210> SEQ ID NO 14
<211> LENGTH: 12
<212> TYPE: PRT
<213> ORGANISM: Porphyromonas gingivalis

<400> SEQUENCE: 14

Gly Gln Asp Glu Met Asn Glu Ile Leu Cys Glu Lys
1               5                   10

<210> SEQ ID NO 15
<211> LENGTH: 9
<212> TYPE: PRT
<213> ORGANISM: Porphyromonas gingivalis

```
<400> SEQUENCE: 15

Cys Tyr Asp Pro Gly Val Thr Pro Lys
1               5

<210> SEQ ID NO 16
<211> LENGTH: 16
<212> TYPE: PRT
<213> ORGANISM: Porphyromonas gingivalis

<400> SEQUENCE: 16

Asp Ala Gly Met Ser Ala Gln Ser His Glu Tyr Cys Val Glu Val Lys
1               5                   10                  15

<210> SEQ ID NO 17
<211> LENGTH: 25
<212> TYPE: PRT
<213> ORGANISM: Porphyromonas gingivalis

<400> SEQUENCE: 17

Glu Gly Leu Thr Ala Thr Thr Phe Glu Glu Asp Gly Val Ala Ala Gly
1               5                   10                  15

Asn His Glu Tyr Cys Val Glu Val Lys
            20                  25

<210> SEQ ID NO 18
<211> LENGTH: 15
<212> TYPE: PRT
<213> ORGANISM: Porphyromonas gingivalis

<400> SEQUENCE: 18

Cys Val Asn Val Thr Val Asn Ser Thr Gln Phe Asn Pro Val Lys
1               5                   10                  15

<210> SEQ ID NO 19
<211> LENGTH: 11
<212> TYPE: PRT
<213> ORGANISM: Porphyromonas gingivalis

<400> SEQUENCE: 19

Cys Gln Ile Leu Ile Glu Asn His Asp Lys Arg
1               5                   10

<210> SEQ ID NO 20
<211> LENGTH: 12
<212> TYPE: PRT
<213> ORGANISM: Porphyromonas gingivalis

<400> SEQUENCE: 20

Tyr Pro Ser Leu Cys Thr Thr Ser Val Ile Gly Lys
1               5                   10

<210> SEQ ID NO 21
<211> LENGTH: 15
<212> TYPE: PRT
<213> ORGANISM: Porphyromonas gingivalis

<400> SEQUENCE: 21

Cys Val Val Asn Ser Pro Gly Gly Gln Thr Ala Ser Met Ala Lys
1               5                   10                  15

<210> SEQ ID NO 22
<211> LENGTH: 13
<212> TYPE: PRT
```

```
<213> ORGANISM: Porphyromonas gingivalis

<400> SEQUENCE: 22

Phe Ser Asn Leu Pro Val Leu Gly Gly Glu Ser Cys Arg
1               5                   10

<210> SEQ ID NO 23
<211> LENGTH: 25
<212> TYPE: PRT
<213> ORGANISM: Porphyromonas gingivalis

<400> SEQUENCE: 23

Phe Val Pro Tyr Asn Asp Asp Glu Gly Gly Glu Glu Glu Asn Val Cys
1               5                   10                  15

Thr Thr Glu His Val Glu Met Ala Lys
            20                  25

<210> SEQ ID NO 24
<211> LENGTH: 15
<212> TYPE: PRT
<213> ORGANISM: Porphyromonas gingivalis

<400> SEQUENCE: 24

Ile Ile Met Glu Leu Ser Glu Ala Asp Val Glu Cys Thr Ile Lys
1               5                   10                  15

<210> SEQ ID NO 25
<211> LENGTH: 20
<212> TYPE: PRT
<213> ORGANISM: Porphyromonas gingivalis

<400> SEQUENCE: 25

Ile Leu His Cys Asn Asn Asn Gln Leu Thr Ala Leu Asn Ser Leu Ser
1               5                   10                  15

Ala Asn Thr Lys
            20

<210> SEQ ID NO 26
<211> LENGTH: 16
<212> TYPE: PRT
<213> ORGANISM: Porphyromonas gingivalis

<400> SEQUENCE: 26

Leu Asp Leu Pro Ala Asn Ala Asp Ile Glu Thr Leu Asn Cys Ser Lys
1               5                   10                  15

<210> SEQ ID NO 27
<211> LENGTH: 19
<212> TYPE: PRT
<213> ORGANISM: Porphyromonas gingivalis

<400> SEQUENCE: 27

Gly Leu Ser Val Leu Val Cys His Ser Asn Gln Ile Ala Gly Glu Glu
1               5                   10                  15

Met Thr Lys

<210> SEQ ID NO 28
<211> LENGTH: 11
<212> TYPE: PRT
<213> ORGANISM: Porphyromonas gingivalis

<400> SEQUENCE: 28

Asn Pro Asn Leu Thr Tyr Leu Ala Cys Pro Lys
```

<210> SEQ ID NO 29
<211> LENGTH: 12
<212> TYPE: PRT
<213> ORGANISM: Porphyromonas gingivalis

<400> SEQUENCE: 29

Met Glu Thr Glu Leu Ala Gln Ile Cys Tyr Ser Lys
1               5                   10

<210> SEQ ID NO 30
<211> LENGTH: 17
<212> TYPE: PRT
<213> ORGANISM: Porphyromonas gingivalis

<400> SEQUENCE: 30

Tyr Asp Ala Ser Asn Glu Leu Arg Pro Thr Ile Leu Cys Ile Tyr Gly
1               5                   10                  15

Lys

<210> SEQ ID NO 31
<211> LENGTH: 19
<212> TYPE: PRT
<213> ORGANISM: Porphyromonas gingivalis

<400> SEQUENCE: 31

Met Asn Ser Asp Glu Leu Phe Glu Glu Ile Thr Tyr Pro Gly Tyr Thr
1               5                   10                  15

Ile Cys Arg

<210> SEQ ID NO 32
<211> LENGTH: 16
<212> TYPE: PRT
<213> ORGANISM: Porphyromonas gingivalis

<400> SEQUENCE: 32

Thr Tyr Met Ile Asp Thr Asn Asp Ser Glu Asn Asp Cys Ile Ala Arg
1               5                   10                  15

<210> SEQ ID NO 33
<211> LENGTH: 17
<212> TYPE: PRT
<213> ORGANISM: Porphyromonas gingivalis

<400> SEQUENCE: 33

Phe Gly Ser Val Leu Glu Val Phe Gln Gln Val Tyr Glu His Glu Cys
1               5                   10                  15

Lys

<210> SEQ ID NO 34
<211> LENGTH: 13
<212> TYPE: PRT
<213> ORGANISM: Porphyromonas gingivalis

<400> SEQUENCE: 34

Glu Glu His Glu Leu Val Cys Ala Ala Ser Thr Leu Lys
1               5                   10

<210> SEQ ID NO 35
<211> LENGTH: 16
<212> TYPE: PRT
<213> ORGANISM: Porphyromonas gingivalis

```
<400> SEQUENCE: 35

Ala Ala Gln Tyr Val Ala Ala His Asp Gly Gln Val Cys Pro Ala Lys
1               5                   10                  15

<210> SEQ ID NO 36
<211> LENGTH: 18
<212> TYPE: PRT
<213> ORGANISM: Porphyromonas gingivalis

<400> SEQUENCE: 36

Arg Pro Val Ser Cys Pro Glu Cys Pro Glu Pro Thr Gln Pro Thr Val
1               5                   10                  15

Thr Arg

<210> SEQ ID NO 37
<211> LENGTH: 16
<212> TYPE: PRT
<213> ORGANISM: Porphyromonas gingivalis

<400> SEQUENCE: 37

Arg Pro Val Ser Cys Pro Glu Cys Pro Glu Val Thr Pro Val Thr Lys
1               5                   10                  15
```